US010155020B2

(12) United States Patent
Xue et al.

(10) Patent No.: US 10,155,020 B2
(45) Date of Patent: *Dec. 18, 2018

(54) COMPOSITIONS AND METHODS FOR TREATING HEPATITIS B

(71) Applicant: The Regents of the University of Colorado, a body corporate, Denver, CO (US)

(72) Inventors: Ding Xue, Louisville, CO (US); Xin Geng, Burlingame, CA (US)

(73) Assignee: The Regents of the University of Colorado, a body corporate, Denver, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 15/343,473

(22) Filed: Nov. 4, 2016

(65) Prior Publication Data

US 2017/0042960 A1 Feb. 16, 2017

Related U.S. Application Data

(63) Continuation of application No. 14/431,622, filed as application No. PCT/US2013/061868 on Sep. 26, 2013, now Pat. No. 9,518,090.

(60) Provisional application No. 61/706,083, filed on Sep. 26, 2012.

(51) Int. Cl.
| | |
|---|---|
| *A61K 38/04* | (2006.01) |
| *C07K 7/06* | (2006.01) |
| *C12N 15/113* | (2010.01) |
| *C07K 7/08* | (2006.01) |
| *G01N 33/50* | (2006.01) |
| *A61K 38/00* | (2006.01) |

(52) U.S. Cl.
CPC ............... *A61K 38/04* (2013.01); *C07K 7/06* (2013.01); *C07K 7/08* (2013.01); *C12N 15/1131* (2013.01); *C12N 15/1135* (2013.01); *G01N 33/5008* (2013.01); *G01N 33/5085* (2013.01); *A61K 38/00* (2013.01); *C12N 2310/14* (2013.01); *C12N 2310/531* (2013.01); *C12N 2320/31* (2013.01); *C12N 2330/50* (2013.01); *G01N 2333/02* (2013.01); *G01N 2500/02* (2013.01); *G01N 2500/10* (2013.01)

(58) Field of Classification Search
CPC .................................. A61K 38/04; C07K 7/06
See application file for complete search history.

(56) References Cited

U.S. PATENT DOCUMENTS 9,518,090 B2 * 12/2016 Xue ........................ A61K 38/04
2017/0042960 A1    2/2017 Xue et al.

FOREIGN PATENT DOCUMENTS

| CN | 101687047 | 3/2010 |
|---|---|---|
| DE | 10238697 | 3/2004 |

OTHER PUBLICATIONS

Shi et al., 2010, Antimicrobial peptaibols, novel suppressors of tumor cells, targeted calcium-mediated apoptosis and autophagy in human hepatocellular carcinoma cells, Molecular Cancer, 9: 26-40.*
English Translation of Official Action for China Patent Application No. 201380059932.7, dated Aug. 23, 2017 3 pages.
Anatol et al., "Expression bcl-2 protein in chronic hepatitis C: Effect of interferon alpha 2b with ribavirin therapy," World Journal of Gastroenterology, 2005, vol. 11(19), pp. 2949-2952.
Arbuthnot et al., "Review, Putative role of hepatitis B virus X protein in hepatocarcinogenesis: Effects on apoptosis, DNA repair, mitogen-activated protein kinase and JAK/STAT pathways," Journal of Gastroenterology and Hepatology, 2000, vol. 15, pp. 357-368.
Geng et al., "Caenorhabditis elegans caspase homolog CSP-2 inhibits CED-3 autoactivation and apoptosis in germ cells," Cell Death & Differentiation, 2009, vol. 16, pp. 1385-1394.
Grynkiewicz, "A New Generation of Ca2+ Indicators with Greatly Improved Fluorescence Properties," Journal of Biological Chemistry, 1985, vol. 260(6), pp. 3440-3450.
Harrison, "Viral membrane fusion," Nature Structure & Molecular Biology, 2008, vol. 15(7), pp. 1094-1101, abstract only, 2 page.
Huang et al., "An immunocompetent mouse model for the tolerance of human chronic hepatitis B virus infection," Proceedings of the National Academy of Sciences, 2006, vol. 103(47), pp. 17862-17867.
Hung et al., "Induction of Bcl-2 Expression by Hepatitis B Virus Pre-S2 Mutant Large Surface Protein Resistance to 5-Fluorouracil Treatment in Huh-7 Cells," PLoS ONE, 2011, vol. 6(12), pp. 1-11.
Klein et al., "Src kinases involved in hepatitis B virus replication," The EMBO Journal, 1999, vol. 18(18), pp. 5019-5027.
Misteli et al., "Applications of the green fluorescent protein in cell biology and biotechnology," Nature Biotechnology, 1997, vol. 15(10), pp. 961-964, abstract only, 1 page.
Shi et al., "Antimicrobial peptaibols, novel suppressors of tumor cells, targeted calcium-mediated apoptosis and autophagy in human hepatocellular carcinaoma cells," Molecular Cancer, 2010, vol. 9(26), pp. 1-15.
Solary et al., "The role of apoptosis in the pathogenesis and treatment of diseases," European Respiratory Journal, 1996, vol. 9, pp. 1293-1305.

(Continued)

*Primary Examiner* — Amber D Steele
(74) *Attorney, Agent, or Firm* — Sheridan Ross P.C.

(57) ABSTRACT

The present invention provides compositions and methods for treating hepatitis B virus (HBV) infection as well as methods for identifying a compound or a composition that is suitable for treating HBV infection. In addition, the present invention provides a suitable non-mammalian animal model that can be used to screen for a compound or a composition that can inhibit HBV replication or treat HBV infection in a mammal. In particular, the present invention provides compositions and methods for treating hepatitis B infection by inhibiting interaction between HBV x protein and a Bcl-2 family protein or by reducing the expression level of a Bcl-2 family protein.

8 Claims, 4 Drawing Sheets

Specification includes a Sequence Listing.

(56) References Cited

OTHER PUBLICATIONS

Terradillos et al., "The hepatitis B virus X protein abrogates Bcl-2-mediated protection against Fas apoptosis in the liver," Oncogene, 2002, vol. 21(3), pp. 377-386.
Zhang et al., "Review Article, Effects of hepatitis B virus X protein on the development of liver cancer," J. Lab. Clin. Med., 2006, vol. 147(2), pp. 58-66.
Official Action and Search Report for Chinese Patent Application No. 201380059932.7, dated Dec. 2, 2016 7 pages.
International Search Report for International (PCT) Patent Application No. PCT/US13/61868, dated Feb. 20, 2014, 4 pages.
International Preliminary Report on Patentability for International (PCT) Patent Application No. PCT/US13/61868, dated Mar. 31, 2015, 6 pages.
Official Action for U.S. Appl. No. 14/431,622, dated Feb. 1, 2016, 15 pages.
Notice of Allowance for U.S. Appl. No. 14/431,622, dated Aug. 30, 2016, 10 pages.

\* cited by examiner

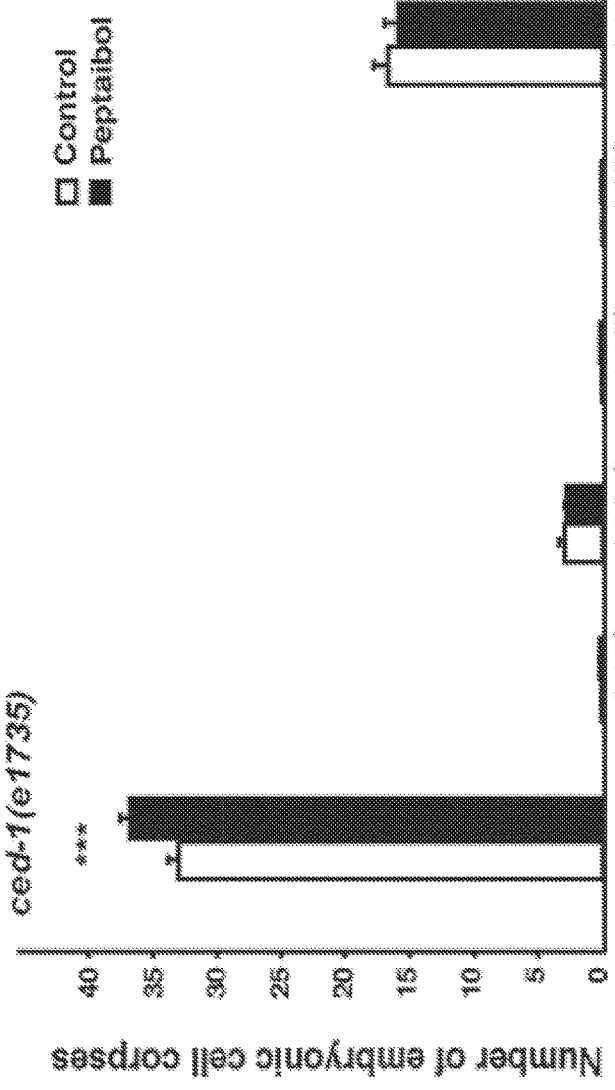

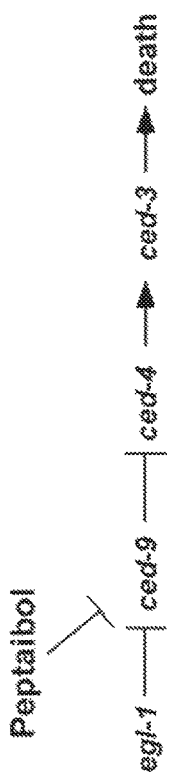
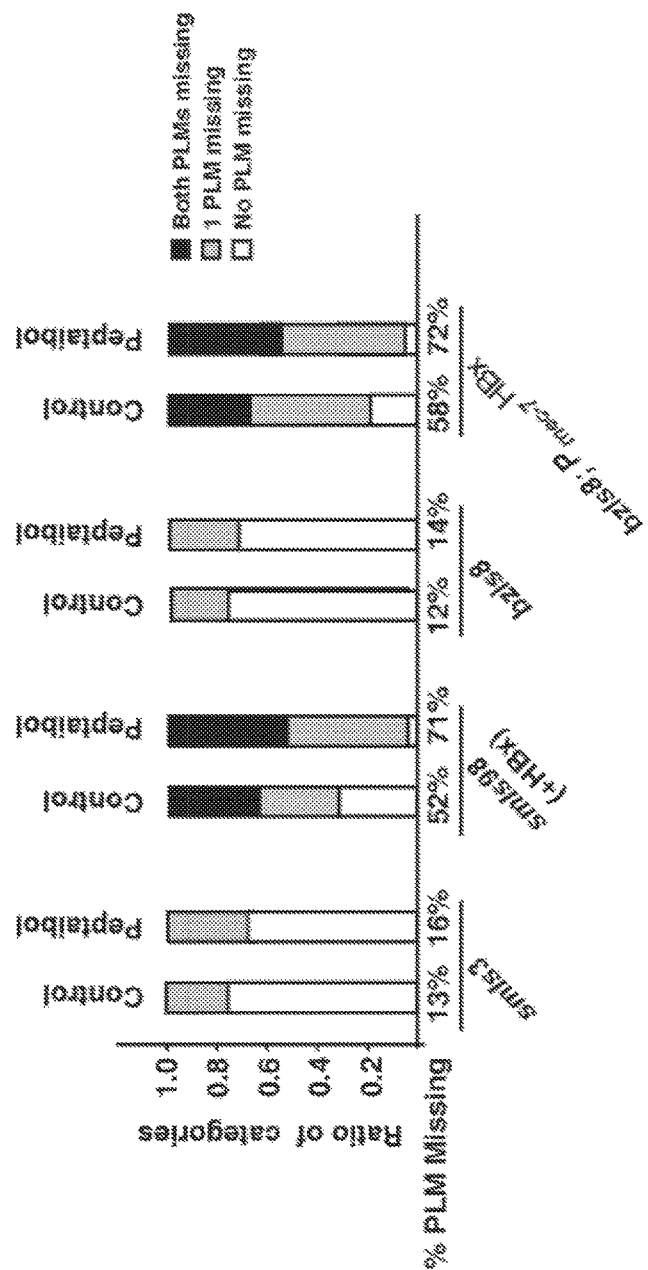
Figure 1f
Figure 2

SEQUENCE LISTING

```
<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: Peptaibol Trichokonin VI
<220> FEATURE:
<221> NAME/KEY: MISC_FEATURE
<222> LOCATION: (1)..(1)
```

```
<223> OTHER INFORMATION: Acetylated 2-aminoisobutyricacid attached
      alanine
<220> FEATURE:
<221> NAME/KEY: MISC_FEATURE
<222> LOCATION: (2)..(3)
<223> OTHER INFORMATION: 2-aminoisobutyricacid attached alanine
<220> FEATURE:
<221> NAME/KEY: MISC_FEATURE
<222> LOCATION: (5)..(5)
<223> OTHER INFORMATION: 2-aminoisobutyricacid attached valine
<220> FEATURE:
<221> NAME/KEY: MISC_FEATURE
<222> LOCATION: (6)..(6)
<223> OTHER INFORMATION: 2-aminoisobutyricacid attached glycine
<220> FEATURE:
<221> NAME/KEY: MISC_FEATURE
<222> LOCATION: (8)..(8)
<223> OTHER INFORMATION: 2-aminoisobutyricacid attached Proline
<220> FEATURE:
<221> NAME/KEY: MISC_FEATURE
<222> LOCATION: (10)..(10)
<223> OTHER INFORMATION: di-(2-aminoisobutyricacid) attached Glutamine

<400> SEQUENCE: 1

Xaa Xaa Xaa Gln Xaa Xaa Leu Pro Val Xaa Gln Phe
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Peptaibol Trichokonin VII
<220> FEATURE:
<221> NAME/KEY: MISC_FEATURE
<222> LOCATION: (1)..(1)
<223> OTHER INFORMATION: Acetylated 2-amininoisobutyric acid attached
      alanine
<220> FEATURE:
<221> NAME/KEY: MISC_FEATURE
<222> LOCATION: (2)..(3)
<223> OTHER INFORMATION: 2-amininoisobutyric acid attached alanine
<220> FEATURE:
<221> NAME/KEY: MISC_FEATURE
<222> LOCATION: (5)..(5)
<223> OTHER INFORMATION: 2-amininoisobutyric acid attached Valine
<220> FEATURE:
<221> NAME/KEY: MISC_FEATURE
<222> LOCATION: (6)..(6)
<223> OTHER INFORMATION: 2-amininoisobutyric acid attached Glycine
<220> FEATURE:
<221> NAME/KEY: MISC_FEATURE
<222> LOCATION: (8)..(8)
<223> OTHER INFORMATION: 2-amininoisobutyric acid attached Proline
<220> FEATURE:
<221> NAME/KEY: MISC_FEATURE
<222> LOCATION: (10)..(10)
<223> OTHER INFORMATION: 2-amininoisobutyric acid attached isovaleric
      acid

<400> SEQUENCE: 2

Xaa Xaa Xaa Gln Val Gly Leu Pro Val Xaa Gln Phe
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Peptaibol Trichokonin VIII
<220> FEATURE:
<221> NAME/KEY: MISC_FEATURE
<222> LOCATION: (1)..(1)
<223> OTHER INFORMATION: Acetylated 2-aminoisobutyric acid attached
      alanine
```

```
<220> FEATURE:
<221> NAME/KEY: MISC_FEATURE
<222> LOCATION: (2)..(2)
<223> OTHER INFORMATION: 2-aminoisobutyric acid attached alanine
<220> FEATURE:
<221> NAME/KEY: MISC_FEATURE
<222> LOCATION: (3)..(3)
<223> OTHER INFORMATION: di(2-aminoisobutyric acid) attached glutamine
<220> FEATURE:
<221> NAME/KEY: MISC_FEATURE
<222> LOCATION: (4)..(4)
<223> OTHER INFORMATION: 2-aminoisobutyric acid substituted valine
<220> FEATURE:
<221> NAME/KEY: MISC_FEATURE
<222> LOCATION: (5)..(5)
<223> OTHER INFORMATION: 2-aminoisobutyric acid substituted glycine
<220> FEATURE:
<221> NAME/KEY: MISC_FEATURE
<222> LOCATION: (7)..(7)
<223> OTHER INFORMATION: 2-aminoisobutyric acid substituted proline
<220> FEATURE:
<221> NAME/KEY: MISC_FEATURE
<222> LOCATION: (9)..(9)
<223> OTHER INFORMATION: di(2-aminoisobutyric acid) substituted
      glutamine

<400> SEQUENCE: 3

Xaa Xaa Xaa Xaa Xaa Leu Xaa Val Xaa Gln Phe
1               5                   10

<210> SEQ ID NO 4
<211> LENGTH: 20
<212> TYPE: DNA
<213> ORGANISM: Artificial Sequence
<220> FEATURE:
<223> OTHER INFORMATION: Primer set 1 for HBS

<400> SEQUENCE: 4
gtgtctgcgg cgttttatca                                              20

<210> SEQ ID NO 5
<211> LENGTH: 21
<212> TYPE: DNA
<213> ORGANISM: Artificial Sequence
<220> FEATURE:
<223> OTHER INFORMATION: Primer Set 1 for HBS

<400> SEQUENCE: 5
gacaaacggg caacatacct t                                            21

<210> SEQ ID NO 6
<211> LENGTH: 23
<212> TYPE: DNA
<213> ORGANISM: Artificial Sequence
<220> FEATURE:
<223> OTHER INFORMATION: Primer set for polymerase

<400> SEQUENCE: 6
tactagtgcc atttgttcag tgg                                          23

<210> SEQ ID NO 7
<211> LENGTH: 21
<212> TYPE: DNA
<213> ORGANISM: Artificial Sequence
<220> FEATURE:
<223> OTHER INFORMATION: Primer set for polymerase

<400> SEQUENCE: 7
cacgatgctg tacagacttg g                                            21
```

```
<210> SEQ ID NO 8
<211> LENGTH: 21
<212> TYPE: DNA
<213> ORGANISM: Artificial Sequence
<220> FEATURE:
<223> OTHER INFORMATION: mRNA Sequence of Bcl-2 targeted by shRNA

<400> SEQUENCE: 8
ccgggagata gtgatgaagt a                                              21

<210> SEQ ID NO 9
<211> LENGTH: 21
<212> TYPE: DNA
<213> ORGANISM: Artificial Sequence
<220> FEATURE:
<223> OTHER INFORMATION: Bcl-xL mRNA targeted by shRNA

<400> SEQUENCE: 9
gtggaactct atgggaacaa t                                              21
```

COMPOSITIONS AND METHODS FOR TREATING HEPATITIS B

CROSS-REFERENCE TO RELATED APPLICATIONS

This application is a continuation of U.S. patent application Ser. No. 14/431,622, filed Mar. 26, 2015 (now U.S. Pat. No. 9,518,090) which is a 35 USC § 371 National Stage of PCT Application No. PCT/US13/61868, filed Sep. 26, 2013, claims the priority benefit of U.S. Provisional Application No. 61/706,083, filed Sep. 26, 2012, each of which is incorporated herein by reference in its entirety.

STATEMENT REGARDING FEDERALLY FUNDED RESEARCH

This invention was made with government support under grant numbers GM059083, GM079097 and GM088241 awarded by the National Institutes of Health. The government has certain rights in the invention.

FIELD OF THE INVENTION

The present invention relates to compositions and methods for treating hepatitis B virus (HBV) infection. In particular, the present invention relates to compositions and methods for treating hepatitis B infection by modulating interaction between HBV x protein and a Bcl-2 family protein or by reducing the expression level of a Bcl-2 family protein.

BACKGROUND OF THE INVENTION

Hepatitis B Virus (HBV) infects more than 400 million people in the world and is the leading cause of hepatocellular carcinoma (HCC) and other liver disease. It has been a major health issue in many countries. Although the current HBV vaccine can prevent new HBV infections, there is no effective treatment for chronic HBV carriers, many of whom will eventually develop various liver disorders and HCC.

Studies have shown that one of the key pathogenic and oncogenic proteins encoded by HBV is the 17-kDa HBV x protein (HBx). HBx is a multi-functional HBV protein that has shown to be crucial for HBV infection and pathogenesis and a contributing cause of hepatocyte carcinogenesis. As appropriately implied by its name, HBx is an enigmatic protein that can bind to a vast number of proteins in various in vitro systems. Unfortunately, the exact host targets and mechanisms of action of HBx are poorly characterized. In fact, to date it has been a major challenge to identify cellular targets of HBx and its mechanisms of action. Because of HBx's role in HBV infection and pathogenesis, it is believed that identification of specific cellular targets of HBx will provide important therapeutic potential in treating chronic HBV carriers.

Accordingly, there is a need to identify cellular target(s) or ligand(s) of HBx. In addition, there is a need for treating HBV infection by targeting cellular target(s) of HBx.

SUMMARY OF THE INVENTION

Some aspects of the invention are based on the discovery by the present inventors that human anti-apoptotic proteins, Bcl-2 and Bcl-xL, are host targets of HBx. In addition, the present inventors have discovered that interactions between HBx and Bcl-2, Bcl-xL, or both are required to stimulate cytosolic calcium elevation, HBV viral replication, and cell death induction. These discoveries by the present inventors of Bcl-2 proteins as the host targets of HBx-induced viral replication and host cell death are useful in identifying and/or producing compositions for the treatment of chronic HBV patients.

Studies have shown that patients with high HBV viral DNA titers are more likely to develop HCC. Thus, in some embodiments of the invention, discoveries by the present inventors can be used to significantly reduce HBV replication, and therefore the likelihood of developing HCC. In fact, discoveries disclosed herein by the present inventors can be used to treat various clinical conditions associated with HBV infection by, for example, significantly reducing the HBV replication. Exemplary clinical conditions that can be treated by compositions and methods of the invention include, but are not limited to, host inflammation induce by HBV-activated necrosis and apoptosis, cirrhosis, HCC, and hepatitis.

In some embodiments, compositions of the invention bind to the Bcl-2 homology 3 (BH3)-like motif (i.e., BH3-domain) of HBx, Bcl-2 or Bcl-xL, or another Bcl-2 family member.

BRIEF DESCRIPTION OF THE DRAWINGS

FIG. 1a shows peptaibol TK sequence alignment. The red rectangles highlight the minor differences among the sequences.

FIG. 1d is a bar graph showing chemical genetic analysis of the peptaibol TK target in the core apoptosis pathway in C. elegans. Peptaibol TK treatment was performed on the following cell death mutants: ced-1 (e1735), ced-1(e1735); egl-1(n3082), ced-1(e1735); ced-9(n1950gf), ced-1(e1735); ced-4(n1162), ced-1(e1735); ced-3(n2433), and ced-1 (e1735) smIs111; ced-4(n1162). smIs111 is an integrated transgene carrying $P_{egl-1}$acCED-3. Two-fold stage embryos were scored in each experiment.

FIG. 1f is a schematic illustration showing interaction of peptaibol TK with the core apoptosis pathway in C. elegans. Peptaibol TK likely induces and enhances apoptosis upstream of or in parallel to EGL-1.

FIG. 2 is a graph showing peptaibol TK enhances HBx-induced cell death in C. elegans. Two different HBx transgenic animals, smIs98 and bzIs8; smEx($P_{mec-7}$HBx), and two control transgenic animals lacking HBx expression, smIs3 and bzIs8, were treated with 5 μM of Peptaibol TK. smIs98 is an integrated transgene containing $P_{mec-3}$GFP and $P_{mec-7}$HBx. smIs3 is an integrated transgene containing $P_{mec-3}$GFP, which directs GFP expression in ten C. elegans sensory neurons, including the PLM touch receptor neurons. bzIs8 is an integrated transgene containing $P_{mec-4}$GFP, which directs GFP expression in six *C. elegans* touch receptor neurons, including the PLM neurons. The presence of GFP-positive PLM neurons was scored using a Nomarski microscope. The data are shown in three categories: both PLM missing (black bars), one PLM missing (gray bars) and no PLM missing (white bars). The y axis represents percentage of each category. Percentage numbers under columns indicate the total PLM missing percentage in each experiment. More than 40 animals were scored in each experiment.

DETAILED DESCRIPTION OF THE INVENTION

Figure 1B:
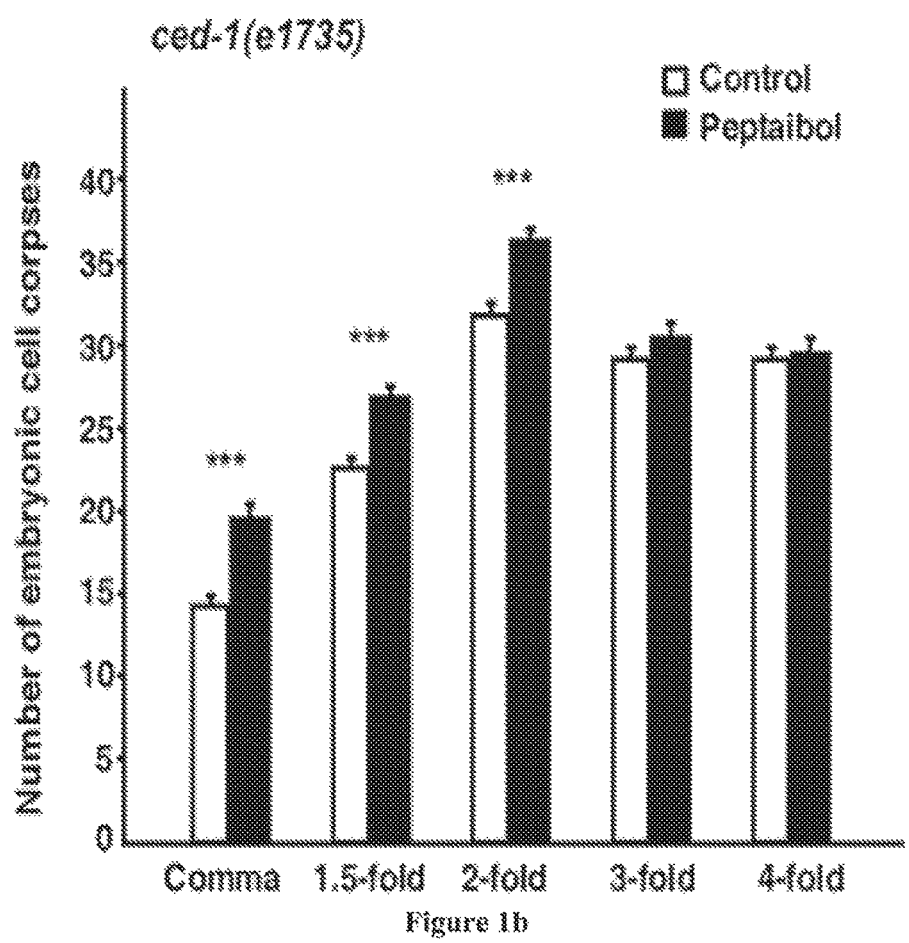
FIG. 1b is a bar graph showing peptaibol TK causes more persistent cell corpses in ced-1(e1735) embryos. Stages of embryos examined were comma, 1.5-fold, 2-fold, 2.5-fold, 3-fold, and 4-fold. The y axis represents average number of cell corpses scored and error bars represent SEM.

Infection with the hepatitis B virus (HBV) can lead to a variety of clinical condition including, but not limited to, the development of hepatitis, liver inflammation, cirrhosis, and hepatocellular carcinoma (HCC). HBV infection is a leading cause of morbidity and mortality worldwide. HBV X protein (HBx) is an important effector for HBV pathogenesis, but its cellular targets and acting mechanisms to date have remained elusive. Disclosed herein is a discovery by the present inventors that HBx interacts with the anti-apoptotic proteins Bcl-2 and Bcl-xL through a Bcl-2 homology 3 (BH3)-like motif in mammalian hepatocytes. The present inventors have also observed that mutations in the BH3-like motif that prevent HBx binding to Bcl-2 and Bcl-xL abrogated cytosolic calcium elevation and cell death induced by HBx expression in hepatocytes and severely impaired HBV replication. The greatly reduced HBV replication caused by mutations in the BH3-like motif of HBx can be substantially rescued by restoring cytosolic calcium. These results show that HBx binding to Bcl-2 family members and subsequent elevation of cytosolic calcium are important for HBV viral replication.

Moreover, RNA interference knockdown of Bcl-2 or Bcl-xL resulted in reduced calcium elevation induced by HBx and decreased viral replication in hepatocytes. These results further indicate that HBx targets Bcl-2 proteins through its BH3-like motif to promote cytosolic calcium elevation, cell death, and viral replication during HBV pathogenesis. Accordingly, some aspects of the invention provide methods for treating HBV infection by (i) inhibiting binding of HBx with a Bcl-2 family protein, (ii) reducing the expression of a Bcl-2 family protein; or (iii) a combination thereof.

HBV is a hepatocyte-specific DNA virus, which encodes several different viral proteins, including DNA polymerase, surface antigen, core antigen, and the X protein (HBx). While the functions of the other viral genes in HBV DNA replication and virion assembly are better understood, the roles and mechanisms of HBx in HBV infection and pathogenesis remain enigmatic. HBx has been implicated in mediating multiple viral and cellular events in HBV-infected cells, including viral replication, transactivation of transcription factors, signal transduction, cell cycle progression, and cell death. Although HBx is found in both the cytoplasm and the nucleus, mitochondria appear to be an important site for HBx action, because expression of HBx has been shown to induce aggregation of mitochondria, loss of mitochondrial membrane potential, and cytochrome c release.

HBx is necessary for viral pathogenesis and oncogenesis in HBV-infected livers. The HBx gene has been shown to be one of the most frequently integrated viral sequences in HCC. In fact, HBx protein is detected in most patients with HBV-related HCC, even in the absence of viral DNA replication. In some cases, HBV variants carrying mutations in HBx have been identified in HCC tissues. Such mutations have resulted in the loss of HBx-dependent activities, indicating that evolving HBx functions may underlie HBV-related liver disease. It has also been shown that HBx promotes liver tumorigenesis in transgenic mice lacking the other components of the HBV virion. Thus, it is clear that HBx plays an important role in the development of HBV-related HCC.

Calcium signaling has been shown to be important for a variety of HBx activities. For example, HBx-induced elevation of cytosolic calcium has been shown to be important for HBV DNA replication, HBV core assembly, and activation of several transcriptional events and signaling cascades. Induction of apoptosis or necrosis by HBx also requires increased cytosolic calcium and mitochondria permeability transition (MPT), a process by which mitochondria regulate cellular calcium during homeostasis and cell death. However, to date the cellular targets with which HBx interacts to induce MPT and cytosolic calcium increase have not been identified.

Many proteins were found to interact with HBx in various in vitro systems. However, most of these protein interactions have not been confirmed in conditions that recapitulate HBV infection in hepatocytes. Genetic redundancy of complex mammalian systems has been a major hurdle to definitive identification of HBx cellular targets. Using a genetically tractable *C. elegans* animal model, the present inventors have discovered that HBx interacts directly with the Bcl-2 homolog, CED-9, to induce cytosolic calcium increase and cell death, mimicking two important events downstream of HBx expression in hepatocytes. In addition, the present inventors have discovered that HBx interacts with two Bcl-2 family members (Bcl-2 and Bcl-xL) in hepatocytes to induce cytosolic calcium elevation, cell death, and viral DNA replication.

The HBV X gene, one of the four coding genes in the HBV genome, encodes a multi-functional protein (HBx) that is essential for HBV infection and replication. HBx also affects multiple cellular events in infected cells, including transcription, signal transduction, proteasome activity, cell cycle progression, and cell death. HBx has also been shown to play an important role in neoplastic transformation of hepatocytes in HBV-infected patients. Even in transgenic mice expressing only HBx, high incidences of liver tumors were found indicating a causal relationship between HBx and HCC.

Studies have linked HBx expression to the activation of necrosis and apoptosis in hepatocytes. HBx can sensitize liver cells to cell death by various insults, including tumor necrosis factor-α (TNF-α) and growth factor deprivation. HBx has also been shown to induce mitochondria aggregation, loss of mitochondrial membrane potential, and cytochrome c release, indicating that HBx may act through mitochondria to induce cell death. Apoptosis and necrosis are also early events of liver pathogenesis in HBx transgenic mice and can lead to development of cirrhosis and HCC. While these results suggest a hepatotoxic function for HBx, to date the cellular targets and signaling pathways that HBx exploits to promote cell death and the development of HCC have remained unclear. Without being bound by any theory, it is believed that chronic hepatocyte cell death causes cycles of inflammatory cytokine release, local liver damage, and compensatory regeneration, leading to the continual acquisition of oncogenic mutations and the development of HCC. Therefore, identification of cellular targets and pathways that mediate HBx-induced cell death can lead to therapeutically effective treatment of HBV-related clinical conditions including a variety of liver diseases.

Calcium signaling has been shown to play an important role in a wide variety of HBx activities. For example, HBx has shown to be responsible for triggering cytosolic $Ca^{2+}$ increase in HBV-infected hepatocytes, which is required for HBV DNA replication. HBx-induced elevation of cytosolic $Ca^{2+}$ is also important for HBV core assembly, some HBx-activated transcriptional events, and activation of several signaling cascades, including JNK and MAPK pathways. HBx has also been shown to modulate cell death by altering cytosolic $Ca^{2+}$. Although it has been suggested that HBx targets mitochondria and mitochondria permeability transition (MPT) in $Ca^{2+}$ regulation, the cellular target(s) with which HBx interacts to alter cytosolic $Ca^{2+}$ has been unknown until the discovery by the present inventors, which is disclosed herein.

Given the complexity of HBx study in mammals, the present inventors have used a simple, genetically tractable animal model *C. elegans* to identify HBx targets and signaling pathways. As disclosed herein, the present inventors discovered that the human Bcl-2 homolog, CED-9, is the cellular target that HBx interacts with to induce cytosolic $Ca^{2+}$ increase and cell apoptosis.

One particular aspect of the invention provides a method for treating hepatitis B infection in a subject. Such a method comprises administering to a subject in need of such a treatment a composition (i) that is capable of inhibiting binding of hepatitis B virus X protein to a Bcl-2 family member protein in the subject; (ii) that is capable of reducing the expression of Bcl-2 family member protein in the subject; or (iii) a combination thereof. It should be noted that the term "treating" or "treatment" of a disease includes: (1) preventing the disease, i.e., causing the clinical symptoms of the disease not to develop in a subject that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms. The term "inhibiting" a protein refers to a decrease in the level or magnitude of an activity or expression of the protein. For example, inhibition of Bcl-2 protein includes reduction in Bcl-2 gene transcription, Bcl-2 gene translation, and/or Bcl-2 protein activity. Inhibition of a particular protein by a composition can be readily determined using any of the methods known to one skilled in the art, e.g., by determining any parameter that is indirectly or directly affected by the expression of the gene encoding that protein or by determining the activity of the protein. Such parameters include, but are not limited to, changes in RNA or protein levels, changes in protein activity, changes in product levels, changes in downstream gene expression, changes in reporter gene transcription (luciferase, CAT, β-galactosidase, β-glucuronidase, green fluorescent protein (see, e.g., Mistili & Spector, Nature Biotechnology 15:961-964 (1997)); changes in signal transduction, phosphorylation and dephosphorylation, receptor-ligand interactions, second messenger concentrations (e.g., cGMP, cAMP, IP3, and Ca2+), and cell growth.

In some embodiments, the Bcl-2 family member protein comprises Bcl-2, Bcl-xL, another Bcl-2 member, or a combination thereof.

Still in other embodiments, the composition comprises a binding inhibitor that is capable of inhibiting binding of hepatitis B virus X protein to said Bcl-2 family member protein. Such binding inhibitor can be a small organic molecule or a drug, small peptides, small RNA molecules such as aptamers, antibodies, siRNA (short inhibitory RNA), or a short hairpin RNA (shRNA) that reduces the expression of the corresponding gene, such as those disclosed in the Examples section. In addition, other suitable shRNAs that can inhibit expression of Bcl-2 family member protein can be readily determined using the procedures described herein. Synthesis of such suitable shRNAs is well known and is often achieved using any of the commercially available automatic oligonucleotide synthesizers. Small organic molecules (e.g., less than 1 kD in molecular weight) that can inhibit the activity Bcl-2 family member protein can also be readily determined using the assay techniques disclosed herein. Furthermore, small organic molecules that can inhibit binding of HBx to a Bcl-2 family member protein can also be readily identified using the methods disclosed herein as well as using a computer-aided simulation. Synthesis of suitable small organic molecules is well known to one skilled in the art. Such compounds can be prepared as an array of chemicals and screened for active compounds. In some embodiments, an antibody that can inhibit binding of HBx to a Bcl-2 family member protein is used to treat HBV infection. In some instances, the composition of the invention comprises an antibody that can target Bcl-2 homology 3 (BH3)-like motif of hepatitis B virus X protein, Bcl-2 family member protein or a combination thereof is used. A suitable antibody for inhibiting binding of HBx to a Bcl-2 family member protein can be readily prepared by one skilled in the art having read the present disclosure using any of the known antibody producing methods.

Yet in other embodiments, the binding inhibitor is capable of interacting with Bcl-2 homology 3 (BH3)-like motif of hepatitis B virus X protein. As disclosed herein, it has been discovered by the present inventors that HBx binds to Bcl-2 and Bcl-xL through its Bcl-2 homology 3 (BH3)-like motif. Accordingly, by targeting the BH3-like motif of HBx, or the BH3-binding pocket in Bcl-2 or Bcl-xL, one can inhibit the binding of HBx to Bcl-2 and/or Bcl-xL.

Still in other embodiments, the composition comprises an expression inhibitor that is capable of reducing the expression of Bcl-2 family member protein. Such expression inhibition can be achieved at the transcription level, translation level, or both. In some particular embodiments, the expression inhibitor is a shRNA that is capable of reducing the expression of Bcl-2, Bcl-xL, another Bcl-2 family member, or a combination thereof.

Another aspect of the invention provides a method for reducing replication of hepatitis B virus (HBV) in a cell infected with HBV. Such a method typically comprises contacting the HBV infected cell with a composition (i) that is capable of inhibiting binding of hepatitis B virus X protein to a Bcl-2 family member protein in said subject; (ii) that is capable of reducing the expression of Bcl-2 family member protein in said subject; or (iii) a combination thereof. As discussed above, suitable binding inhibitors and expression inhibitors can be readily determined and synthesized by one skilled in the art having read the present disclosure.

Still another aspect of the invention provides a method for reducing the level of cytosolic calcium elevation in a cell, such as hepatocyte, infected with hepatitis B virus (HBV). Such a method generally includes contacting the HBV infected cell with a composition (i) that is capable of inhibiting binding of hepatitis B virus X protein to a Bcl-2 family member protein in said subject; (ii) that is capable of reducing the expression of Bcl-2 family member protein in said subject; or (iii) a combination thereof. As discussed above, suitable binding inhibitors and expression inhibitors can be readily determined and synthesized by one skilled in the art having read the present disclosure.

Other aspect of the invention includes a method for identifying a composition that is capable of treating hepatitis B virus (HBV) infection in a mammal. It should be noted that currently there is no suitable animal model for a relatively rapid molecular genetic analysis of HBV known to one skilled in the art. However, as disclosed herein the present inventors have discovered that CED-9 protein of *C. elegans* comprises the similar binding domain to HBx as that of Bcl-2 family member proteins in human. Accordingly, the method for identifying a composition that is capable of treating HBV infection in a mammal includes determining the effect of a particular composition in an interaction between HBV X protein and CED-9 protein of *C. elegans*. In general, if a reduction in the interaction between HBV X protein and CED-9 protein in the presence of the composition is observed, then it is an indication that that particular composition is capable of treating HBV infection in a mammal.

Another aspect of the invention provides a method for treating HBV infection in a subject by administering a therapeutically effective amount of a peptaibol. "Peptaibols" are a large group of short polypeptides named after their three characteristic structural features: peptide, Aib (α-aminoisobutyric acid), and C-terminal amino alcohol. They contain a high proportion of unusual amino acids, especially Aib, and are found as secondary metabolites of fungi that have high similarity in amino acid sequences among fungi species. Since the discovery of Alamethicin, the first member of peptaibols, in 1967, to date more than 300 peptaibols have been identified.

Most peptaibols affect biological processes of both microorganisms and animal cells and cause cell death of human cultured cells. They often are inserted into the plasma membrane and oligomerize to form ion-permeable channels, leading to sharp voltage changes and death of the treated cells. In a large family of peptaibols, Trichokonins (TK) were first isolated and purified from *Trichoderma pseudokoningii*. Without being bound by any theory, it is believed that like other peptaibols, peptaibol TK inserts into lipid membrane and forms an ion-channel through oligomer formation. When human tumor cells were treated with peptaibol TK, these cells showed characteristic apoptosis features, indicating that peptaibol TK promotes apoptotic cell death. A recent study showed that treatment of hepatocellular carcinoma (HCC) with peptaibol TK caused both apoptosis and autophagic death through a calcium-mediated mechanism. However, the cellular target of peptaibol TK remains unclear.

Programmed cell death or apoptosis is a highly conserved cellular process across the animal kingdom. Genetic analysis of programmed cell death in the nematode *C. elegans* has been instrumental in identifying crucial apoptosis regulators and effectors, leading to the identification of a conserved cell-killing pathway. Without being bound by any theory, it is believed that in this cell killing pathway, EGL-1, a homolog of the human BH3-only pro-apoptotic proteins, initiates apoptosis by binding to CED-9, a homolog of the human Bcl-2 cell death inhibitors, leading to the disassociation of CED-4, a homolog of the human apoptotic protease activator Apaf-1, from the inhibitory CED-4/CED-9 complex tethered on the outer membrane of mitochondria. The released CED-4 then oligomerizes to induce proteolytic activation of the CED-3 zymogen, a homolog of the human caspases, many of which have been shown to be involved in either apoptosis initiation or execution. The highly conserved nature of the apoptosis pathway is demonstrated by the findings that human Bcl-2 protein can partially substitute for the function of CED-9 in *C. elegans* and that a human viral protein, the hepatitis B virus X protein (HBx) containing a BH3-like motif, can induce both apoptosis and necrosis in both *C. elegans* and human hepatocytes by directly targeting CED-9 and Bcl-2 family proteins.

Recently, *C. elegans* has emerged as a powerful animal model for drug screens and subsequent target identification. For example, studies in *C. elegans* reveal that the Benzenoid chemicals, including naphthalene and para-dichlorobenzene, target caspases in both *C. elegans* and humans to inhibit apoptosis, resulting in cell death abnormality in worms and tumorigenesis in human.

Some aspects of the invention are based on the discovery by the present inventors that peptaibol TK promotes apoptosis in *C. elegans*. Without being bound by any theory, it is believed that peptaibol TK promotes apoptosis by targeting the cell death inhibitor CED-9, thus leading to increased CED-4 release from the inhibitory CED-9/CED-4 complex in cooperation with EGL-1. Other aspects of the invention are based on the discovery by the present inventors that peptaibol TK enhances HBx-induced cell death in *C. elegans*, in HBV transgenic mice, and in human hepatocytes. These results show that peptaibol TK is a potential antitumor drug that can also be used to treat HBV infection. In some embodiments, peptaibol TK comprises peptaibol TK VI (SEQ ID: NO 1), peptaibol TK VII (SEQ ID: NO 2) or peptaibol TK VIII (SEQ ID: NO 3).

It should be appreciated that the scope of the invention also includes a derivative or a modified peptaibols. As used herein, a "derivative" of peptaibol refers to a modified peptaibol in which one or more amino acid in the peptide of peptaibol of interest is replaced with a functionally similar amino acid. For example, naturally occurring residues are divided into groups based on common side chain properties:

(1) hydrophobic: norLeucine, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Thus, in general, a modified peptaibol refers to a peptaibol in which one or more, typically five or less, often three or less and more often two or less amino acids of a peptaibol of interest have been replaced with an amino acid having a similar side chain property. For example, "a derivative" of peptaibol TK refers to a homolog, an analog of peptaibol TK. Exemplary derivatives of peptaibol TK include, but are not limited to:

(i) a peptaibol whose peptide fragment is derived from peptaibol TK that contains α-aminoisobutyric acid and an alcohol and have a similar activity (i.e., in vitro assay activity within ±25%, typically within ±10%, and often within ±5% activity;
(ii) peptaibol in which one or several amino acids of the natural peptaibol TK sequence have been substituted by other amino acids;
(iii) peptaibol modified at the N- and/or C-terminal end of the peptide sequence of peptaibol TK, for example, by substitution; thus, esters and amides can be considered as derivatives;
(iv) peptaibol TK peptides the modification of which prevents their destruction by proteases or peptidases, as well as to peptide-PEG-conjugates derived from the basic sequence of peptaibol or its fragment;

(v) modified peptides of peptaibol TK which are derived from the chain of peptaibol TK peptide or its fragment and wherein one or several of the amino acids of the sequence have been substituted by genetically encoded or not genetically encoded amino acids or peptidomimetics;

(vi) peptides of peptaibol TK having conservative substitutions of amino acids as compared to the natural sequence of peptaibol TK in one or several positions. A conservative substitution is defined as the side chain of the respective amino acid being replaced by a side chain of similar chemical structure and polarity, the side chain being derived from a genetically coded or not genetically coded amino acid. Families of amino acids of this kind having similar side chains are known in the art. They comprise for instance amino acids having basic side chains (lysine, arginine, histidine), acidic side chains (aspartic acid, glutamic acid), uncharged polar side chains (glycine, aspartamic acid, glutamine, serine, threonine, tyrosine, cysteine), non-polar side chains (alanine, valine, leucine, isoleucine, proline, phenylalanine, methionine, tryptophan), β-branched side chains (threonine, valine, isoleucine) and aromatic side chains (tyrosine, phenylalanine, tryptophane, histidine). Such conservative substitutions of side chains are typically carried out in non-essential positions. In this context, an essential position in the sequence is one wherein the side chain of the relevant amino acid is of significance for its biological effect.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Example 1

Immunoprecipitation assays. HepG2 cells transfected with the pcDNA3.1-Flag-HBx constructs or the pHBV replicons (wild-type and G124L/I127A mutations) were lysed and precipitated using an anti-Flag antibody or an anti-HBx antibody. The proteins pulled down with HBx were detected by either immunoblotting analysis or mass-spectrum analysis.

Calcium imaging and analysis. HepG2 cells co-transfected with pcDNA3-mCherry and pcDNA3.1-Flag-HBx constructs (wild-type or G124L/I127A mutations) were incubated for 35 min with 4 μM Fura-2-AM and 0.04% Pluronic solution 48 hr post transfection, washed three times with buffer, and incubated for an additional 15 min to allow for cleavage of the acetoxymethyl (AM) ester, which trapped Fura-2 in the cells. Data were collected using the Metafluor software and analyzed by Excel. Statistical analysis was performed using t-test in KaleidaGraph program. The error bars indicate SEM (standard error of the mean).

Quantification of HBV DNA replication and HBcAg. Southern hybridization analysis and quantitative real-time PCR were used to quantify the amount of HBV replication DNA intermediates isolated from HepG2 cells or from mouse livers. The level of cytoplasmic HBcAg was measured by chemiluminescence using a commercial assay kit.

Hydrodynamic injection. 30 μg of the pHBV replicon and 3 μg of pcDNA3-GFP were injected into the tail veins of Balb/c mice within 5 seconds in a volume of PBS equivalent to 10% of the mouse body weight. Livers of the injected mice were assayed for HBcAg and viral DNA two days after injection.

Molecular Biology. The HBx cDNA clone was obtained from Dr. Xiao-Kun Zhang (The Burnham Institute for Medical Research). Standard methods of cloning, sequencing, and polymerase chain reaction amplification (PCR) were employed. To make HBx mammalian expression constructs, a DNA fragment encoding Flag-HBx was amplified by PCR and subcloned into the pcDNA3.1(+) vector via its Nhe I and EcoR V sites. The HBx mutant constructs containing G124L and I127A substitutions were generated using a Quick-Change Site-Directed Mutagenesis kit (Stratagene Inc.) and confirmed by DNA sequencing. The pHBV replicon contains a 140% DNA copy of the HBV genome and replicates in an HBx-dependent manner in HepG2 cells. pHBV containing HBx(G124L, I127A) was made by Quick-Change site-directed mutagenesis and confirmed by DNA sequencing.

Cell Culture. Human HepG2 cells were grown in DMEM with 10% fetal bovine serum (FBS; Sigma-Aldrich). Transfection of HepG2 cells was carried out using Effectene Transfection Reagent (Qiagen) following the manufacturer's protocol. A transfection efficiency of 15 to 30% was routinely achieved. All transfection experiments were performed 24 hours after plating. 1 μg of pcDNA3.1, pcDNA3.1-Flag-HBx, or pcDNA3.1-Flag-HBx(G124L, I127A) was diluted in 100 μl of the DNA-condensation buffer (Buffer EC) supplied by the manufacturer (Qiagen). 8 μl of enhancer and 10 μl of Effectene were sequentially added to the mixture, each followed by vortexing and incubation at room temperature per manufacture protocol. After that, the mixture was supplemented with 0.6 ml complete medium and added to cells. Co-transfection of an enhanced GFP (EGFP)-expressing plasmid pEFGP-C1 (1 μg) was included, where appropriate, to monitor transfection efficiency when performing flow cytometry analysis in the cell killing assays.

Co-Immunoprecipitation Assays. Co-immunoprecipitation experiments were performed using an antibody (M2) to the Flag epitope (Sigma) or an anti-HBx antibody (16F9). Briefly, HepG2 cells transfected with pcDNA3.1-Flag-HBx or pHBV constructs (wild-type or mutant) were lysed in lysis buffer (100 mM NaCl, 0.5 mM $MgCl_2$, 0.15 mM $CaCl_2$, 1% (v/v) NP-40, 10 mM Tris-HCl, pH 8.0) containing protease inhibitor cocktail tablets (Roche). Cell debris was removed by centrifugation at 10,000 g for 10 minutes at 4° C. The cell lysate was precleared with Protein G Sepharose beads (GE healthcare) and subsequently incubated with the M2 or 16F9 antibody for 1 hour with gentle shaking at 4° C. Protein G Sepharose beads were then added and the incubation continued for another 2 hours. The beads were washed five times with the lysis buffer. The bound proteins were resolved on a 15% SDS polyacrylamide gel and detected by immunoblotting using anti-Bcl-2, anti-Bcl-xL, and anti-Mcl-1 antibodies (Cell Signaling Technology), respectively.

Flow Cytometry. 36 hours post-transfection, living and dead HepG2 cells were scraped into the cell growth medium and precipitated by centrifugation. Cells from one well of a six-well plate (~6×$10^5$ cells) were washed in cold PBS twice and resuspended in 600 μl Annexin V-binding buffer (10 mM HEPES, 140 mM NaCl, and 2.5 mM $CaCl_2$, pH 7.4). Labeling of cells by Propidium Iodide (Sigma) and Annexin-V pacific blue (Invitrogen) was carried out according to the protocol provided by Invitrogen. Briefly, 100 μl of the suspended cells were transferred to a new tube. 5 µl of Annexin-V Pacific Blue (Invitrogen) and 5 µl of Propidium Iodide (Sigma) were added to each tube and incubated for 30 minutes at room temperature in the dark. 400 µl of Annexin V-binding buffer were then added to each tube. Cells were analyzed on the CyAn™ ADP Analyzer (DakoCytomation) with background gates set to exclude non-transfected GFP (−) cells and to restrict Annexin-V Pacific Blue staining alone, or Propidium Iodide staining alone, to fewer than 0.5% positive events. Data were collected from more than 10,000 cells for each sample.

Cytosolic Calcium Measurement. HepG2 cells were co-transfected with pcDNA3-mcherry and pcDNA3.1-Flag-HBx constructs (wild-type or mutant) using lipofectamine LTX (Invitrogen). After 48 hours or later, cells were washed with the HHBSS buffer (Hank's Balanced Salt Solution supplemented with 20 mM HEPES and 11 mM Glucose) three times and then incubated with 4 µM Fura-2-AM and 0.04% Pluronic solution for 35 minutes. Cells were rinsed with HHBSS three times and left with HHBSS for another 15 minutes to allow for cleavage of the acetoxymethyl (AM) ester, trapping Fura-2 inside the cells.

Imaging experiments were performed on an Axiovert 200M inverted fluorescence microscope (Zeiss) with a Cascade 512B CCD camera (Roper Scientific), equipped with a Xenon Arc lamp (XBO75), and 340/26 and 380/10 excitation filters, a 450 nm dichroic mirror, and a 535/45 emission filter. Excitation and emission filters were placed in filter wheels external to the microscope controlled by a Lambda 10-3 filter changer (Sutter Instruments) to allow for rapid acquisition of ratio images. Images were collected using Metafluor software (Universal Imaging). All images were collected on healthy cells with similar mCherry intensity using a 40× oil objective and were background corrected by generating a region of interest (ROI) on a blank area of the coverslip and subtracting the fluorescence intensity of each excitation channel. The background corrected intensities at 340 nM and 380 nM excitation were used to calculate the Fura-2 340/380 ratio.

To determine the resting [$Ca^{2+}$] in the cytosol, cells were treated with 5 µM ionomycin and 5 mM EGTA in $Ca^{2+}$-free HBSS to obtain the ratio of the unbound indicator ($R_{min}$). Cells were then washed with $Ca^{2+}$-free HBSS for three times and treated with 5 µM ionomycin and 10 mM $Ca^{2+}$ in HBSS to obtain the ratio of the calcium-saturated indicator ($R_{max}$). $Ca^{2+}$ concentrations were calculated using the reported $K_d$ value of Fura-2 and the experimentally derived R, $R_{min}$, $R_{max}$, $S_f$ and $S_b$ (the emission intensity at 380 nm for $Ca^{2+}$-free and $Ca^{2+}$-bound Fura-2, respectively) in each individual cell according to the following equation:

$$[Ca^{2+}] = K_d \times \frac{(R - R_{min})}{(R_{max} - R)} \times \frac{S_f}{S_b}.$$

Details on the microscope, sensor calibration, and conversion of Fura-2 ratios into $Ca^{2+}$ concentrations have been described in *J Biol Chem.*, 1985, 260, 3440-3450. The results were presented as the fold-increase of the calcium concentration in cells transfected with pcDNA3-Flag-HBx over that in cells transfected with the empty vector.

Southern Blot Analysis. HepG2 cells (3×10 cm plate per sample) transfected with the pHBV replicon (wild-type or mutant) were washed twice with cold phosphate-buffered saline (PBS) and lysed in 750 µl NET buffer (50 mM Tris-HCl pH 7.5, 1 mM EDTA, 100 mM NaCl, 0.5% Nonidet P-40) per 10 cm plate for 1 hour. HepG2 cell lysates were clarified by centrifugation at 12000 g for 30 minutes at 4° C. The supernatant was adjusted to 6 mM $CaCl_2$ and treated with 100 µg/ml of Micrococcal nuclease for 30 minutes at 37° C. The reaction was stopped by addition of EDTA to a final concentration of 25 mM. Proteins were digested with 0.2 mg/ml proteinase K and 0.5% SDS for overnight at 37° C. Nucleic acids were purified by phenol/chloroform extraction and ethanol precipitation. After centrifugation at 12000 g for 30 minutes at 4° C., the pellet was resuspended in 10 µl TE buffer. DNA samples were resolved on a 1.2% agarose gel, transferred to nylon membrane (Bio-Rad), and hybridized with a digoxin-labeled DNA fragment covering the entire HBx gene.

Northern Blot Analysis. Total cellular RNA was extracted from transfected cells using the Trizol reagent (Invitrogen) according to the manufacturer's instructions. 20 µg of RNA were separated on 1% denaturing formaldehyde agarose gel, transferred onto nylon membranes, and hybridized to probes covering the whole HBV genome, prepared as described above.

Quantitative Real-Time PCR Analysis. Intracellular HBV replicating intermediates were isolated from cytoplasmic viral core particles as described in *EMBO J.*, 1999, 18, 5019-5027. The pHBV plasmid was used as the standard for quantification and serial dilutions from $2 \times 10^8$ to 200 IU/ml were prepared. The primer sequences for quantitative PCR were chosen carefully from regions coding for HBV S antigen and Polymerase. Sequences of primer Set 1 (corresponding to HBS): forward primer: 5'-GTGTCTGCG-GCGTTTTATCA-3' (SEQ ID: NO 4), reverse primer: 5'-GACAAACGGGCAACATACCTT-3' (SEQ ID: NO 5). Primer Set 2 (corresponding to Polymerase): forward primer: 5'-TACTAGTGCCATTGT-TCAGTGG-3' (SEQ ID: NO 6), reverse primer: 5'-CACGATGCTGTACAGACT-TGG-3' (SEQ ID: NO 7). Real-time PCR analyses were performed using a SYBR Green Premix Ex Taq Kit (Takara Bio) in an ABI Prism 7500 PCR system (Applied Biosystems). PCR products were analyzed by fluorescence. Each standard dilution was subjected to 2 PCR runs in at least two independent experiments. Based on the mean threshold cycles ($C_T$) for each dilution, a linear regression was carried out with the $C_T$ values as a function of the decadic logarithm of the number of template molecules per reaction. Least-squares regression analysis, performed by the ABI prism 7500, plotted $C_T$ as a function of nominal input number. The measured raw copy number from each reaction was calculated using the $C_T$ value of each PCR interpolated against the linear regression of the standard curve. Each DNA specimen was subjected to 4 PCR runs with at least three independent experiments.

HBV Core Antigen Analysis. The amounts of HBcAg were determined by chemiluminescence using a commercial assay kit (Wantai, Beijing, China).

Mice. Balb/c mice (male, 6 to 7 weeks old) were divided into two groups (6 mice for each injection group). 30 µg of the pHBV replicon (wild-type or mutant) plus 3 µg of pcDNA3-GFP were injected into the tail veins of mice within 5 seconds in a volume of PBS equivalent to 10% of the mouse body weight. Livers of these mice were collected and assayed for the levels of HBcAg and viral DNA, respectively, two days after injection as described in *Proc Natl Acad Sci USA.*, 2006, 103, 17862-17867.

shRNA-Mediated Knockdown in HepG2 Cells. Validated Mission® shRNA lentiviral particles targeting human Bcl-2 or the control shRNA lentiviral particles were obtained from the Functional Genomic Facility of the University of Colorado. A short hairpin RNA targeting human Bcl-xL was produced using the lentivirus-based shRNA delivery vector pLL3.7-neo. Viral particles targeting Bcl-xL were produced in HEK 293FT cells and used to infect HepG2 cells. For shRNA knockdown experiments, cells were plated 24 hours before infection. Lentiviral particles were added in the presence of hexadimethrine bromide at the recommended multiplicity of infection. Infected cells were selected in media with puromycin (1 µg/mL; Sigma-Aldrich) or neomycin (0.5 mg/mL; Sigma-Aldrich). The Bcl-2 mRNA sequence targeted by the shRNA is: 5'-CCGGGAGATAGT-GATGAAGTA-3' (SEQ ID: NO 8). The Bcl-xL mRNA sequence targeted by the shRNA is: 5'-GTGGAACTC-TATGGGAACAAT-3' (SEQ ID: NO 9).

Results

Analyses of HBx activities in *C. elegans* by the present inventors showed that HBx interacts with CED-9 in *C. elegans* to induce cytosolic calcium increase and cell death. Moreover, HBx also interacted with human Bcl-2 and Bcl-xL in vitro through its BH3-like motif and this interaction was disrupted by two substitutions in conserved residues of the BH3-like motif (G124L and I127A). The present inventors also conducted experiments to determine whether HBx interacts with Bcl-2 and/or Bcl-xL in human hepatic HepG2 cells by the co-immunoprecipitation assay. In HepG2 cells transfected with pcDNA3.1-Flag-HBx, endogenous Bcl-2 and Bcl-xL, but not the anti-apoptotic Bcl-2 family member Mcl-1, were co-precipitated with Flag-HBx using an antibody to the Flag epitope. In contrast, no Bcl-xL and only a trace amount of Bcl-2 were co-precipitated with Flag-HBx (G124L, I127A), which was expressed in HepG2 cells at a comparable level to Flag-HBx. These results indicate that HBx associates with Bcl-2 and Bcl-xL in human cells through its BH3-like motif. Importantly, in HepG2 cells transfected with a 140% head-to-tail DNA copy of the HBV genome (pHBV) with or without HBx(G124L, I127A) mutations, endogenous Bcl-2 and Bcl-xL, but not Mcl-1, were co-precipitated with HBx, but not with HBx(G124L, I127A), using an antibody to HBx. Therefore, HBx expressed from its native promoter in a replicating HBV genome associates with endogenous Bcl-2 and Bcl-xL in human hepatic cells through its BH3-like motif.

The cell-killing activity of HBx in human cells was analyzed by staining HBx-transfected HepG2 cells with Annexin-V Pacific Blue and propidium iodide (PI) to distinguish living cells from apoptotic and necrotic cells. Flow cytometry analysis of cells transfected with pcDNA3.1-Flag-HBx showed 10.6% apoptotic cells (Annexin-V positive and PI negative) and 7.9% necrotic cells (Annexin-V positive and PI positive). Significantly less cell death was observed in HepG2 cells transfected with the same amount of pcDNA3.1-Flag-HBx(G124L, I127A) (4.87% apoptotic cells and 1.14% necrotic cells) or empty pcDNA3.1 vector (1.14% apoptotic cells and 0.32% necrotic cells). Therefore, as in *C. elegans*, HBx utilizes its BH3-like motif to bind anti-apoptotic Bcl-2 and Bcl-xL proteins and induces both apoptosis and necrosis in human hepatocytes.

Since calcium signaling is an important event downstream of HBx, whether the BH3-like motif of HBx is necessary for HBx-induced elevation of cytosolic calcium was examined. Cytosolic calcium in HepG2 cells transfected with pcDNA3.1-Flag-HBx or pcDNA3.1-Flag-HBx(G124L, I127A) was determined using the ratiometric fluorescent calcium indicator Fura-2. It was found that the resting calcium concentration was significantly increased upon expression of HBx compared to the vector-only control, whereas expression of HBx(G124L, I127A) failed to do so. It is believed that the HBx-induced calcium elevation was not due to increased cell death, because a similar level of calcium increase was observed in the presence of Z-VAD, a pan-caspase inhibitor that blocks cell death. These results indicate that HBx can induce an increase in cytosolic calcium that is dependent on its BH3-like motif and association with Bcl-2 family proteins.

Given the role of HBx in HBV DNA replication, whether interactions between HBx and Bcl-2 proteins are important for HBV replication was examined. Cytoplasmic viral core particles, where HBV DNA replication occurs, were isolated from HepG2 cells transfected with the pHBV replicon with or without the HBx(G124L, I127A) mutations. The level of HBV DNA replication was examined by southern blot analysis. Compared with cells transfected with wild-type pHBV, HBV DNA replication was significantly reduced in cells transfected with the mutant pHBV. The level of the HBV core protein (HBcAg), which correlates with the level of HBV DNA, was also greatly reduced in cells transfected with the mutant HBV genome. Northern blot analysis showed no reduction in HBV pregenomic (pg)/precore (pc) RNA, preS/S mRNA, or HBx mRNA in cells transfected with the mutant pHBV replicon. Quantitative real-time polymerase chain reaction (Q-PCR) analysis of isolated viral particles revealed a 8-9 fold reduction in HBV DNA replication in cells transfected with the mutant HBV genome compared with cells transfected with the wild-type HBV genome. These results indicate that the BH3-like motif of HBx is critical for HBV DNA replication but dispensable for HBV transcription. Interestingly, HBV DNA replication in cells transfected with the mutant HBV genome was largely rescued by treatment with 5 µM ionomycin, an ionophore that increases cytosolic calcium. This result shows that increased cytosolic calcium is an important signaling event downstream of HBx interaction with Bcl-2 proteins that stimulates HBV DNA replication.

The role of HBx interaction with Bcl-2 proteins for HBV replication was examined in an established mouse model of chronic HBV infection. The pHBV replicon with wild-type HBx or HBx(G124L, I127A) was introduced into BALB/C mice (n=6) through hydrodynamic tail vein injection, along with a pcDNA3-GFP reporter as a control for injection efficiency. Cytoplasmic viral core particles were isolated from the liver 2 days after injection and subjected to southern blot analysis. The average level of replicative DNA intermediates in livers of mice receiving the mutant pHBV replicon was reduced by 2-3 fold compared to that of mice receiving the wild-type pHBV replicon. Expression of intrahepatic HBV core antigen (HBcAg) was similarly reduced in mice receiving the mutant pHBV replicon. These results confirm the role of the BH3-like motif of HBx, and thus the association of HBx with Bcl-2 family proteins, for HBV DNA replication in HBV-infected liver.

The role of Bcl-2 proteins for HBV replication was determined by knocking down the expression of Bcl-2 or Bcl-xL in HepG2 cells through RNA interference (RNAi). Compared with control short hairpin RNA (shRNA), Bcl-2 and Bcl-xL shRNA significantly reduced the expression of Bcl-2 and Bcl-xL in HepG2 cells. Q-PCR analysis of isolated viral particles revealed a 21-41% reduction in HBV DNA replication in cells infected by lentivirus expressing Bcl-2 or Bcl-xL shRNA, compared to cells with control shRNA. Overexpression of the anti-apoptotic Mcl-1 protein, which does not interact with HBx, in cells treated with Bcl-2 or Bcl-xL shRNA did not significantly prevent reduction of HBV DNA replication, indicating that decreased HBV DNA replication caused by loss of Bcl-2 or Bcl-xL is unlikely due to impaired survival of the host cells. Moreover, RNAi knockdown of Bcl-2 or Bcl-xL dampened but did not completely eliminate intracellular calcium increase induced by HBx, which is consistent with the finding that Bcl-2 or Bcl-xL knockdown reduced but did not block HBV DNA replication and indicates that Bcl-2 and Bcl-xL are partially redundant in mediating HBx functions. Bcl-2 and Bcl-xL double knockdown cells were not viable for analysis of HBV viral replication and intracellular calcium changes. These results indicate that Bcl-2 and Bcl-xL are important for HBV viral replication, and together with the findings described above, provide strong evidence that HBx targets both Bcl-2 and Bcl-xL to increase intracellular calcium and to promote HBV DNA replication.

Discussion

Despite the role of HBx in HBV pathogenesis and oncogenesis, identification of HBx host targets has remained a major challenge in the last three decades. The intricacy of HBx activities, the lack of a suitable animal model to study HBV infection, variability among cell culture assays, and the complexity of the mammalian genome, which encodes at least six Bcl-2 family proteins, have all contributed to the longstanding questions regarding the functions of HBx, its interactions with host targets, and its mechanisms of action. The present inventors have engineered a C. elegans animal model to identify HBx targets and downstream signaling pathways (see Example 2). Mimicking the initial cellular events that unfold following liver infection by HBV, HBx induced both apoptosis and necrosis in C. elegans through canonical cell death pathways. Interestingly, a unique gain-of-function mutation (G169E) in the Bcl-2 homolog CED-9, which inhibits cell death in C. elegans by blocking the binding of the endogenous BH3-only cell death inducer EGL-1 to CED-9, also completely blocked the interaction between CED-9 and the BH3-like motif of HBx and HBx-induced cell death in C. elegans. Remarkably, Bcl-2 can fully substitute for CED-9 in C. elegans to mediate HBx-induced cell killing, indicating that Bcl-2 likely interacts with HBx in mammals. The present inventors have demonstrated here that HBx associates with Bcl-2 and Bcl-xL in human hepatocytes through its BH3-like motif and that this protein interaction is crucial for HBx-induced cytosolic calcium elevation, cell death, and viral DNA replication. These findings indicate that molecular mimicry of endogenous BH3-only proteins by HBx enables its interactions with conserved host targets and hijacking of cell signaling pathways to benefit viral infection.

Calcium signaling is a critical event downstream of HBx expression that promotes inter alia HBV replication, core assembly, cell death, and other HBx functions. HBx has been hypothesized to effect mitochondria permeability transition (MPT), which is important for intracellular calcium homeostasis and cell death. Importantly, both Bcl-2 and Bcl-xL are mitochondrial proteins and have been implicated in regulating MPT. HBx binding to Bcl-2 and Bcl-xL is critical for calcium regulation by HBx, since expression of HBx, but not HBx(G124L, I127A), which fails to bind Bcl-2 and Bcl-xL, triggered elevation of cytosolic calcium in hepatocytes. The finding that G124L/I127A mutations in the BH3-like motif of HBx greatly reduced HBV DNA replication in human and mouse hepatocytes, which can be substantially rescued by restoring cytosolic calcium with ionomycin, and the observation that RNAi knockdown of either Bcl-2 or Bcl-xL significantly compromised HBx-induced intracellular calcium increase and HBV replication, provided further confirmation that HBx targets Bcl-2 proteins to trigger cytosolic calcium elevation required for HBV replication and other events such as cell death.

Hepatocarcinogenesis is a complex and poorly understood process. Chronic hepatocyte cell death induced by HBV infection or carcinogens may trigger cycles of inflammation, immune response, compensatory tissue regeneration, and the acquisition of oncogenic mutations that lead to development of HCC. On the other hand, hepatocyte expression of pro-survival factors, such as Bcl-2 and p38α kinase, has been shown to be effective in preventing HCC development. Moreover, HBV viral replication plays an important contributing role in hepatocarcinogenesis. The development and progression of HCC in chronic HBV patients strongly correlates to the viral DNA level in a dose-dependent manner. Therefore, blocking HBV viral replication and HBV-induced cell death represents an effective strategy to treat chronic HBV patients and to prevent the development of HCC. The present inventors have discovered that the BH3-like motif of HBx is necessary for HBx binding to Bcl-2 family proteins, which results in elevated cytosolic calcium, efficient viral replication, and HBV-induced cell death. Therefore, therapeutically targeting the BH3-like motif of HBx or the interactions between HBx and Bcl-2 proteins is a new and effective strategy to treat chronic HBV patients and to prevent development of HCC.

Example 2

This example shows inter alia that expression of HBx in C. elegans induces both necrotic and apoptotic cell death, mimicking an early event of liver infection by HBV. Genetic and biochemical analyses indicate that HBx interacts directly with the Bcl-2 homolog CED-9 through a Bcl-2 homology 3 (BH3)-like motif to trigger both cytosolic $Ca^{2+}$ increase and cell death. Importantly, Bcl-2 can substitute for CED-9 in mediating HBx-induced cell killing in C. elegans, suggesting that CED-9 and Bcl-2 are conserved cellular targets of HBx. A genetic suppressor screen of HBx-induced cell death has produced many mutations, including mutations in key regulators from both apoptosis and necrosis pathways, indicating that this screen can identify new apoptosis and necrosis genes. The present inventors have found that C. elegans serve as an animal model for identifying crucial host factors and signaling pathways of HBx and can be used in development of strategies to treat HBV-induced liver disorders.

C. elegans strains and cell death assays. Animals were grown and maintained using standard protocols. Germline transformation was used to generate transgenic C. elegans strains expressing HBx and other genes. Embryonic lethality was scored 24 hours after heat-shock treatment. PLM killing by HBx was scored as described in Nat Struct Mol Biol., 2008, 15, 1094-1101.

GST pull-down assays. GST-HBx proteins were purified using Glutathione Sepharose beads and binding to CED-9 or Bcl-2 family proteins was assayed as described in Nat Struct Mol Biol., 2008, 15, 1094-1101.

Calcium imaging and analysis. A C. elegans strain with an integrated $P_{mec-4}$YC2.12 cameleon transgene (bzIs17) was used to quantify relative cytosolic calcium levels in PLM neurons by the FRET microscopy.

Worm Strains and Culture Conditions. C. elegans strains were cultured at 20° C. using standard procedures. The N2 Bristol strain was used as the wild-type strain. The following alleles were used in the genetic analyses: LGI, mec-6(el 342); LGIII, ced-4(nl 162), clp-1 (tm690), cnx-1 (nr2009), ced-9(nl 950, n2812); LGIV, itr-1 (sa73), ced-3(n2433);

LGV, crt-1 (bz29), unc-68(e540), egl-1 (n3082), cyn-1 (tm4171); LGX, asp-3(tm4559), asp-4(ok2693). Detailed allele information is described in Wormbase (wormbase.org). In addition to these strains, bzIs8 is an integrated transgene located on LGX and contains a $P_{mec-4}$GFP construct, which directs GFP expression in six *C. elegans* touch receptor neurons. smIs98 is an integrated transgene located on LGII and contains $P_{mec-3}$GFP and $P_{mec-7}$HBx constructs. smIs3 is an integrated transgene containing Pmec-3GFP. bzIs17 is an integrated trans gene containing Pmec-4YC2.12, which directs expression of the YC2.12 cameleon calcium sensor under the control of the mec-4 gene promoter. smIs451 is an integrated transgene containing only Pmec-7HBx. All integrated transgenes were backcrossed six times with the N2 strain before being used for further genetic analyses.

Embryonic Lethality Assay. Gravid transgenic adults were placed on plates for 2 hr at 20° C. to let them lay eggs. The plates were then heat-shocked at 33° C. for 1 hr and returned to 20° C. for 1 hr before removing all adult worms. After 24 hr at 20° C., the transgenic embryos were scored for embryonic lethality.

EMS Mutagenesis. EMS mutagenesis was carried out. Briefly, smIs98; smEx[$P_{hsp}$HBx+$P_{hsp}$GFP] L4 larvae were exposed to 47 mM EMS for 4 hr with agitation. The F1 progeny of mutagenized animals were cloned out, and the F2 embryos were subjected to heat-shock treatment at 33° C. for 1 hr and returned to 20° C. for 1 hr. This heat-shock treatment was repeated 3 more times to ensure 100% killing of embryos by HBx. The surviving larvae with robust GFP expression in many cells were identified as putative suppressor mutants, which were subjected to the secondary screen using smIs98. Only those mutants in which HBx-induced touch cell death was completely or partially suppressed were considered as true suppressors and analyzed further.

Quantification of PLM Killings by HBx. PLM neurons were scored in L4 larvae in the presence of the integrated transgene, smIs98 or bzIs8, using a Nomarski microscope equipped with epifluorescence.

Transgenic Worms. Germline transformation was performed as described in *Cell Death Differ.*, 2009, 16, 1385-1394. The $P_{hsp}$HBx constructs (at 25 ng/μl each) were injected into animals with the appropriate genetic background using $P_{sur-5}$GFP (25 ng/μl) as a co-injection marker, which directs GFP expression in all somatic cells in most developmental stages. The $P_{mec-7}$HBx construct or its mutant derivatives (25 ng/μl) was injected into bzIs8; unc-76(e911) animals using p76-16B (5 ng/μl) as a co-injection marker, which rescues the Uncoordinated defect of the unc-76(e911) mutant. The $P_{mec-7}$CED-9, $P_{mec-7}$CED-9ΔTM, or $P_{mec-7}$hBcl-2 construct (25 ng/μl) was injected into smIs98; ced-9(n1950) animals using pRF4 (50 ng/pμl) as a co-injection marker, which causes a Roller phenotype in transgenic animals.

Molecular Biology. Standard methods of cloning, sequencing, and polymerase chain reaction amplification (PCR) were employed. Briefly, full-length HBx cDNA was subcloned into the pGEX-4T-2 vector via its EcoR I and Not I sites to generate the pGEX-4T-2-HBx protein expression vector. To make $P_{hsp}$HBx constructs, full-length HBx cDNA was subcloned into *C. elegans* heat shock vectors, pPD49.78 and pPD49.83, via Nhe I and Kpn I sites. $P_{mec-7}$HBx was constructed by subcloning HBx cDNA into the pPD52.102 vector via its Nhe I and Kpn I sites. The HBx mutant constructs containing G124L, I127A, E125A or E126A substitutions were generated using a QuickChange Site-Directed Mutagenesis kit (Stratagene Inc.) and confirmed by DNA sequencing. To make Bcl-2, Bcl-xL and Bax protein expression vectors, the coding regions for human Bcl-2(1-218), human Bcl-xL(1-209), and mouse Bax(1-173) were amplified by PCR and subcloned into the pET-19b vector via its Nde I and Xho I sites, respectively. pET-24a-CED-9(68-251) and pET-24a-CED-9(68-251; G169E) were generated by Parrish et al. (7). $P_{mec-7}$CED-9 and $P_{mec-7}$hBcl-2 were generated by subcloning the full-length ced-9 and human Bcl-2 cDNA fragments into the pPD52.102 vector via its Nhe I and EcoR V sites, respectively. $P_{mec-7}$CED-9ΔTM was generated by subcloning a cDNA fragment encoding CED-9 amino acids 1-251 into the pPD52.102 vector via its Kpn I and EcoR V sites.

Protein Expression and Purification. GST-HBx proteins (wild-type or mutants) were expressed in *Escherichia coli* strain BL21(DE3). The soluble fraction of the *E. coli* lysate was incubated with Glutathione Sepharose beads (Pharmacia) and purified GST-HBx proteins were eluted with 10 mM reduced glutathione (Amersham). CED-9(68-251), human Bcl-2(1-218), human Bcl-xL(1-209), and mouse Bax(1-173) proteins were expressed individually in BL21(DE3) as either a C-terminally or N-terminally six histidine-tagged protein using a pET-24a or pET-19b vector (Novagen), respectively. They were affinity purified using Talon Metal Affinity Column (Clontech) and eluted with 250 mM imidazole.

GST Fusion Protein Pull-Down Assays. Purified GST-HBx proteins or GST protein (2.5 μg each) immobilized on Glutathione Sepharose beads (Pharmacia) were incubated with 5 g of purified CED-9(68-251)-His$_6$, CED-9(68-251; G169E)-His$_6$, His$_6$-hBcl-2(1-218), His$_6$-hBcl-xL(1-209), or His$_6$-mBax(1-173) in a binding buffer containing 25 mM Tris-HCl (pH 7.5), 150 mM NaCl, 0.1% Nonidet P40, 10% glycerol, 1 mM phenylmethylsulphonyl fluoride, and 5 mM dithiothreitol at 4° C. for 2 hr. One portion of the incubation mix was analyzed by western blot to examine the input levels of GST-HBx proteins and Bcl-2 family proteins using an antibody to GST (B-14) or the six-histidine tag (H15), respectively (Santa Cruz Biotechnology, Inc.). The Sepharose beads were then washed five times with the same buffer before the bound proteins were resolved on a 15% SDS polyacrylamide gel and detected by immunoblotting.

Structural Modeling. Homology modeling of the complex structure between the HBx Peptide (residues 120-128) and CED-9 was performed using the published complex structure between the EGL-1 BH3 domain and CED-9 as a template (PDB code: 1TY4). The model was further optimized using the program COOT manually to be reasonable. Both modeling figures were created by the PyMOL program and labeled using Adobe Illustrator CS4.

Chemical Treatment of *C. elegans*. Worms were treated with chemicals using an oil-base protocol. Briefly, Thapsigargin (Sigma) or Cyclosporin A (Sigma) was dissolved in DMSO and then diluted it in 100% soybean oil (Crisco). L4 larval stage hermaphrodite animals were placed onto standard NGM plates seeded with OP50. Oil solutions containing the chemicals were spread (0.8-1.0 ml) onto each plate so that the NGM surface was completely covered by oil. Worms lived at the interface of the NGM medium and the oil. F1 progeny was examined for PLM cell death or the FRET ratio in PLMs.

Calcium Imaging and Analysis in *C. elegans*. A *C. elegans* strain with an integrated $P_{mec-4}$YC2.12 cameleon transgene (bzIs17) was used to quantify relative cytosolic calcium levels in PLM neurons. Animals at the L1 larval stage were immobilized on a 2% agar pad in a solution containing 0.3 M 2,3-butanedione monoxime and 10 mM HEPES (pH 7.2).

PLM neurons were visualized using an Axioplan 2 Nomarski Microscope (Zeiss) equipped with a SensiCam CCD camera (PCO Imaging Kelheim, Germany). CFP (427/10-25 excitation, 440 dichroic, 472/30-25 emission), YFP (504/12-25 excitation, 520 dichroic, 542/27-25 emission), and FRET (427/10-25 excitation, 440 dichroic, 542/27-25 emission) filters (Semrock), a colliminating emission port adapter (Photometrics), and the Slidebook 5.0 software (Intelligent Imaging Innovations) were used to collect FRET data. The CFP channel collects CFP emission after CFP excitation and the FRET channel collects YFP emission after CFP excitation. Analysis of exported tiff files containing data from the FRET or CFP channel was performed using the ImageJ software (NIH). The FRET ratio was calculated by $(FRET_{PLM}-FRET_{bkgnd})/(CFP_{PLM}-CFP_{bkgnd})$, where $FRET_{PLM}$ and $CFP_{PLM}$ are the mean fluorescent intensities in the FRET and CFP channels of the PLM neuron and $FRET_{bkgnd}$ and $CFP_{bkgnd}$ are the mean fluorescent intensities in the FRET and CFP channels of a background region adjacent to the PLM neurons.

Statistical Analysis. Experimental data are presented as mean±standard error of the mean (SEM). Significance of the differences between two data sets was determined using the Student t test.

Results

To assess the activities of HBx in *C. elegans*, global expression of HBx was induced under the control of the *C. elegans* heat-shock promoters ($P_{hsp}$HBx). Expression of HBx in *C. elegans* had deleterious effects, leading to a high percentage of embryonic lethality. Approximately 97% of $P_{hsp}$HBx transgenic embryos did not hatch and were invariably deformed. Many contained large vacuoles that resembled necrotic cells and raised discs characteristic of apoptotic cells. To determine the nature of HBx-induced cell death, the $P_{hsp}$HBx transgenes was introduced into animals defective in ced-3, which encodes a caspase essential for apoptosis, or animals defective in mec-6, which is important for necrosis. A strong loss-of-function (lf) mutation in ced-3 (n2433) or mec-6 (e1342) partially suppressed embryonic lethality caused by HBx overexpression, indicating that both apoptotic and necrotic cell death contributes to lethality of HBx transgenic embryos.

To analyze the cell-killing activity of HBx, HBx was expressed in six mechanosensory neurons (ALML/R, AVM, PVM, PLML/R) under the control of the mec-7 gene promoter ($P_{mec-7}$HBx). To aid in identification of these nonessential neurons, GFP was expressed under the control of the mec-3 promoter ($P_{mec-3}$GFP), which drives gene expression in the same six touch cells plus four other sensory neurons (PVDL/R and FLPL/R). An integrated transgene (smIs98) containing both $P_{mec-7}$HBx and $P_{mec-3}$GFP was used to assay killing of touch cells by HBx. On average, 13-50% of touch cells in smIs98 animals underwent ectopic cell death, with the two posterior PLM neurons showing most ectopic deaths (50%). PLM death was thus used in all subsequent genetic analysis. Some dying touch cells in smIs98 animals displayed an enlarged vacuolar morphology characteristic of necrotic cells and some displayed the raised disc-like morphology of apoptotic cells. Consistently, cell killing by HBx was partially suppressed by either ced-3 (n2433) or mec-6(e1342) lf mutations and eliminated by loss of both genes. These results confirmed that HBx induces both apoptosis and necrosis in *C. elegans*.

Many genes involved in apoptosis and necrosis have been identified in *C. elegans*. In the apoptotic pathway, four key proteins, EGL-1 (similar to human BH3-only pro-apoptotic proteins), CED-9 (human Bcl-2 proteins), CED-4 (human Apaf-1), and CED-3 (human caspases), act sequentially to control activation of apoptosis. In the necrotic pathway, several conserved endoplasmic reticulum (ER) proteins involved in regulating $Ca^{2+}$ homeostasis, including two $Ca^{2+}$-binding proteins, CRT-1 (calrecticulin) and CNX-1 (calnexin), and two $Ca^{2+}$ channels, ITR-1 (inositol trisphosphate receptor) and UNC-68 (uncoordinated, a ryanodine receptor homolog), control release of $Ca^{2+}$ from ER to cytosol in response to various necrotic insults. $Ca^{2+}$ elevation in cytosol then initiates necrosis through conserved $Ca^{2+}$-dependent proteases, CLP-1 (calpain family) and TRA-3 (transformer), and their downstream aspartyl proteases (ASP-3 and ASP-4). Whether these key components of apoptotic and necrotic cell death pathways affect HBx-induced cell death was examined. Loss of egl-1, ced-3 or ced-4 partially suppressed HBx-induced cell death (from 50% to 22-26% PLM death), indicating that HBx induces cell death partly through the apoptotic pathway. Likewise, loss of crt-1, cnx-1, itr-1, clp-1, tra-3, asp-3 or asp-4 partially suppressed HBx-induced cell killing (from 50% to 12-32% PLM death), indicating that HBx induces cell death in part through the necrotic pathway. Importantly, loss of ced-3 and one of the components in the necrotic pathway (mec-6, clp-1, itr-1, and crt-1) almost completely blocked ectopic touch cell death induced by HBx, indicating that apoptosis and necrosis account for virtually all cell death induced by HBx.

Like loss of egl-1, ced-4 or ced-3, a gain of function (gf) mutation (n1950) in ced-9 prevents most somatic apoptosis in *C. elegans*. However, unlike egl-1(lf), ced-4(lf) and ced-3(lf) mutations that partially block HBx-induced cell death, ced-9(n1950gf) substantially completely inhibited HBx-induced touch cell death and embryonic lethality. Moreover, a strong lf mutation in ced-9 (n2812) substantially completely suppressed ectopic cell-killing induced by HBx in the ced-4(n1162) mutant background, which blocks massive ectopic cell deaths and embryonic lethality caused by ced-9(n2812)(25). These results indicate that HBx induces both apoptotic and necrotic cell death through CED-9.

The ced-9(n1950gf) mutation results in substitution of $Gly^{169}$ by Glu in the BH3-binding pocket of CED-9, which disrupts the binding of the BH3-only protein EGL-1 to CED-9 and prevents EGL-1-induced release of the pro-apoptotic CED-4 dimer from the CED-4/CED-9 complex tethered on the surface of mitochondria. It is believed that HBx acts by binding to CED-9, thereby antagonizing its death inhibitory function. Whether HBx binds CED-9 was examined in vitro using a glutathione S transferase (GST) fusion protein pull-down assay. GST-HBx specifically interacted with CED-9 tagged with a six-histidine epitope but not with the mutant CED-9(G169E) protein. Interestingly, HBx contains a sequence (residues 116-132) that is distantly related to the BH3 motif of many pro-apoptotic BH3-only proteins. The possibility that the interaction of HBx with CED-9 occurs through this motif was tested by altering two amino acids ($Gly^{124}$ to Leu and $Ile^{127}$ to Ala) in HBx that are conserved among BH3-only proteins and that face CED-9 in a structural model of the HBx/CED-9 complex. G124L substitution markedly reduced and I127A substitution compromised the binding of HBx to CED-9 in vitro. Alteration of both residues (G124L; I127A) abolished association of HBx with CED-9. Consistently, in an in vitro CED-4 releasing assay, HBx but not the HBx(G124L; I127A) mutant, was able to release CED-4 from the GST-CED-9/CED-4 complexes tethered to Glutathione resin. When HBx(G124L) or HBx(I127A) was expressed under the control of the mec-7 promoter, both mutant proteins displayed reduced cell killing activity, while the double mutant, HBx(G124L; I127A), induced minimal ectopic touch cell death. Similarly, HBx (G124L; I127A) did not cause embryonic lethality in *C. elegans* like HBx when expressed under the control of the heat-shock promoters. These in vitro and in vive results indicate that association of HBx with CED-9 is required for HBx to induce ectopic cell killing in *C. elegans*.

To characterize further the interaction between HBx and CED-9, structural modeling of the HBx/CED-9 complex was performed using the published EGL-1/CED-9 complex structure, replacing the EGL-1 BH3 helix with the putative BH3 motif of HBx. In the modeled HBx/CED-9 structure, $Glu^{125}$ and $Glu^{126}$ of HBx are in the vicinity of the $Gly^{169}$ residue of CED-9. The replacement of $Gly^{169}$ by a bulky, negatively charged Glu in the ced-9(n1950gf) mutant is expected to cause a steric clash and/or charge repulsion with either $Glu^{125}$ or $Glu^{126}$ or both, disrupting the interaction between HBx and CED-9. Two single Glu to Ala substitutions (E125A and E126A) in HBx was generated and tested whether residues with a neutral, smaller side chain may alleviate steric clash or charge repulsion and restore binding of HBx to CED-9(G169E). Although neither mutation affected binding of HBx to wild-type CED-9, E125A, but not E126A, specifically restored binding of HBx to CED-9 (G169E) in vitro. In vivo, both HBx(E125A) and HBx (E126A) caused ectopic touch cell death and a high percentage of embryonic lethality in wild-type animals like HBx when expressed under the control of the mec-7 and the heat-shock promoters, respectively. However, only HBx (E125A), but not HBx or HBx(E126A), induced robust killing of touch cells and embryo in ced-9(n1950) animals. These results correlate with the observation that HBx (E125A), but not HBx or HBx(E126A), bound CED-9 (G169E) in vitro. Together, they provide strong evidence that HBx induces cell death in *C. elegans* by directly interacting with CED-9.

The functions of CED-9 and Bcl-2 in cell death regulation are highly conserved, and Bcl-2 can partially substitute for ced-9 to inhibit apoptosis in *C. elegans*. Therefore, whether HBx binds Bcl-2 family proteins and if Bcl-2 can substitute for CED-9 in mediating HBx-induced cell killing in *C. elegans* was tested. It was found that GST-HBx specifically interacted with human anti-apoptotic proteins Bcl-2 and Bcl-xL, but not with the pro-apoptotic protein Bax. The binding of HBx to Bcl-2 and Bcl-xL was markedly reduced by the G124L and I127A mutations, indicating that HBx also interacts with Bcl-2 and Bcl-xL in vitro through its BH3-like motif.

HBx was unable to induce touch cell death in ced-9 (n1950) animals owing to its inability to bind CED-9 (G169E). This suppression of HBx-induced cell death was completely reversed by expression of wild-type CED-9 ($P_{mec-7}$CED-9) in smIs98; ced-9(n1950) animals. Importantly, expression of human Bcl-2 in touch cells ($P_{mec-7}$hBcl-2) also completely restored HBx-induced cell killing in smIs98; ced-9(n1950) animals, indicating that HBx interactions with Bcl-2 and CED-9 and the ensuing signaling mechanisms are conserved.

Since HBx acts through CED-9 to induce necrosis and because cytosolic $Ca^{2+}$ increase is essential for activation of necrosis in *C. elegans*, whether HBx targets CED-9 to affect intracellular $Ca^{2+}$ was examined. A *C. elegans* strain carrying an integrated transgene (bzIs17) that expresses a cameleon $Ca^{2+}$ sensor under the control of the mec-4 gene promoter was used to monitor intracellular $Ca^{2+}$ in six touch cells through the fluorescence-resonance energy transfer (FRET) assay. In this assay, the FRET ratio (defined as the fluorescence intensity in the FRET channel divided by the intensity in the CFP channel) is indicative of relative cytosolic $Ca^{2+}$ concentrations. bzIs17 animals were treated with thapsigargin, which inhibits the ER ATPase that pumps $Ca^{2+}$ from the cytosol into the ER and is expected to result in elevation of cytosolic $Ca^{2+}$. Indeed, the FRET ratio in PLM neurons of thapsigargin-treated animals was significantly higher than that of untreated or vector-treated animals. To assess the impact of HBx expression on cytosolic $Ca^{2+}$ in living cells, the asp-3(tm4559) mutation was used to block most of the touch cell deaths (from 50% missing PLMs to 12%) induced by an integrated $P_{mec-7}$HBx transgene (smIs451). Loss of asp-3 on its own did not alter cytosolic $Ca^{2+}$, as the FRET ratios of bzIs17 and bzIs17; asp-3 (tm4559) animals were almost identical. However, in bzIs17; asp-3(tm4559); smIs451 animals, a 40% increase in the FRET ratio was observed, indicating that HBx expression in touch cells caused a significant increase in cytosolic $Ca^{2+}$. Importantly, the HBx-induced $Ca^{2+}$ increase was obliterated by the ced-9(n1950) mutation, which prevents HBx binding to CED-9. Therefore, it appears HBx directly targets CED-9 to induce cytosolic $Ca^{2+}$ increase in *C. elegans*.

CED-9 has been shown to localize to the outer membrane of mitochondria through its C-terminal transmembrane (TM) domain. A CED-9 mutant (CED-9ΔTM) lacking this TM domain fails to localize to mitochondria and is found in the cytoplasm. Interestingly, expression of CED-9ΔTM still partially rescues defects in apoptosis and embryonic lethality in ced-9(lf) animals, indicating that mitochondrial localization is not essential for CED-9 to inhibit apoptosis in *C. elegans*. Whether mitochondrial localization is important for CED-9 to mediate HBx-induced cell killing was examined. Expression of CED-9ΔTM in touch cells ($P_{mec-7}$CED-9ΔTM) only restored PLM killing in smIs98; ced-9(n1950) animals to 7-9%, compared to 46-52% PLM killing caused by expression of wild-type CED-9. These results indicate that mitochondrial localization is critical for CED-9 to mediate HBx-induced cell killing.

Because mitochondrial permeability transition (MPT) has been implicated in mediating HBx-induced $Ca^{2+}$ increase, whether MPT affects HBx-induced cell killing and $Ca^{2+}$ increase in *C. elegans* was tested. smIs98 animals were treated with cyclosporin A (CsA), a peptide that desensitizes MPT by inhibiting the activity of the mitochondrial cyclophilin D, the essential regulatory component of MPT. In smIs98 animals that normally lost 50% of PLM neurons, CsA treatment reduced the percentage of missing PLM to 15%. Similarly, a deletion mutation (tm4171) in cyn-1, which encodes the *C. elegans* cyclophilin D homolog, reduced the percentage of missing PLM in smIs98 animals to 17%. These results indicate that MPT is likely involved in HBx-induced cell killing. Moreover, loss of ced-3 enhanced suppression of HBx-induced cell killing by CsA (from 15% PLM death in CsA-treated animals to 4% PLM death, whereas loss of either clp-1 or mec-6 did not. These results suggest that MPT is critical for HBx-induced necrotic cell death and provide the first report that MPT is important for necrosis in *C. elegans*.

Whether MPT is involved in HBx-induced cytosolic $Ca^{2+}$ increase was examined. The FRET ratio of bzIs17; asp-3 (tm4559); smIs451 animals treated with CsA was reduced to the level seen in bzIs17; asp-3(tm4559) animals, indicating that HBx-induced cytosolic $Ca^{2+}$ increase was completely suppressed by CsA. Therefore, HBx-induced $Ca^{2+}$ increase is likely mediated by MPT, which is consistent with observations from human cells.

To identify targets or effectors of HBx-induced cell killing, a genetic screen was conducted to isolate suppressors of the embryonic lethality phenotype caused by global expression of HBx. To facilitate identification of true HBx suppressors, the screen was performed in smIs98 animals that co-expressed HBx and GFP under the control of the heat-shock promoters ($P_{hsp}$HBx and $P_{hsp}$GFP). $P_{hsp}$GFP was used to eliminate mutations that affected transcription from the heat-shock promoters, while smIs98 provided a secondary screen for true suppressors of HBx-induced cell killing. From a screen of approximately 20,000 haploid genomes, 31 HBx-induced death suppressors were isolated, which were named hids mutations. Most hids mutations not only suppressed embryonic lethality caused by global expression of HBx ($P_{hsp}$HBx) but also reduced or blocked ectopic neuronal death in smIs98 animals, suggesting that they affect either the apoptotic or the necrotic pathway or both. Indeed, one mutation (sm250) failed to complement clp-1(tm690) and is a nonsense allele of clp-1 ($Trp^{295}$ to Opal). Another hids mutant (sm221) failed to complement mec-6(e1342) and is a missense allele of mec-6 ($Gly^{77}$ to Ser). The third hids mutant (sm224) had no apoptotic cell corpse and is a nonsense allele of ced-4 ($Glu^{383}$ to Ochre). These findings indicate that the genetic suppressor screen successfully identified genes involved in HBx-induced apoptosis and necrosis and is a powerful tool to identify new apoptosis and necrosis genes and additional effectors or targets of HBx.

Discussion

HBV infects more than 350 million people and is the leading cause of liver disease and HCC worldwide. As the key pathogenic and oncogenic protein encoded by HBV, HBx presumably interacts with host factors to promote virus replication and various pathogenic consequences, such as liver cell death and HCC. However, the host targets of HBx and its mechanisms of action remain elusive, partly due to the lack of a suitable animal model amenable to genetic analysis, inconsistencies often associated with cell culture studies, and the genetic complexity of mammalian systems (e.g., mammals have at least six Bcl-2-like cell death inhibitors). These technical hurdles have prevented definitive identification of HBx cellular targets in the last three decades. Therefore, development of a simpler animal model where HBx host factors and downstream effectors can be identified and verified through powerful molecular genetic approaches becomes imperative for understanding HBx functions and treating HBV patients.

The present inventors have discovered that C. elegans, with its much simpler genome (only one Bcl-2 homolog) and powerful genetic tools, presents one such animal model. The present inventors' finding that expression of HBx in C. elegans induces both apoptosis and necrosis, which mimics one of the early cellular events following liver infection by HBV, leads to systematic genetic dissection of HBx-induced cell death pathways that involve highly conserved cell death regulators and executors. These include key regulators of apoptosis (CED-9, CED-4, and CED-3) and critical components in the necrosis pathway, especially those involved in regulating $Ca^{2+}$ signaling, including ER $Ca^{2+}$ binding proteins and channels (CRT-1, CNX-1, UNC-68 and ITR-1), $Ca^{2+}$-dependent proteases (CLP-1 and TRA-3), and MPT, many of which previously have not been implicated in HBV or HBx-induced pathogenesis. MPT, however, has been implicated in HBx-induced cell killing and HBV replication in humans. CED-9, a key apoptosis regulator, was discovered unexpectedly to be a host target of HBx in cell death and $Ca^{2+}$ signaling in C. elegans, which led to identification of human Bcl-2 proteins as conserved host targets of HBx-mediated $Ca^{2+}$ stimulation and HBV replication in human hepatocytes. These findings demonstrate the validity of the C. elegans model for studying HBV and HBx. The HBx suppressor screen has identified important regulators of both cell death pathways and still has the potential to identify new targets or effectors of HBx as well as new apoptosis and necrosis genes.

Importantly, the cell killing activity of HBx is dependent on CED-9, a Bcl-2 homolog and a key cell death inhibitor, because a gain-of-function mutation (G169E) in the BH3-binding pocket of CED-9 blocks HBx-induced cell death in C. elegans. In vitro, HBx interacts with CED-9, but not with CED-9(G169E), through its BH3-like motif. Alteration of two conserved residues in the BH3-like motif of HBx abolishes binding of HBx to CED-9 and HBx's cell killing activity. A compensatory mutation (E125A) in the BH3-like motif of HBx that restores binding of HBx to CED-9 (G169E) allows HBx to kill efficiently in ced-9(n1950gf) animals. These in vitro and in vivo results establish that HBx interacts directly with CED-9 through its BH3-like motif to induce cell killing, and that CED-9 is the bona fide cellular target of HBx. Importantly, HBx interacts with Bcl-2 and Bcl-xL, two human anti-apoptotic CED-9 homologs, through the same BH3-like motif in human hepatocytes and this interaction is critical for HBx-induced cytosolic $Ca^{2+}$ elevation, cell death, and HBV viral replication. These results and the finding that Bcl-2 can fully substitute for CED-9 in C. elegans to mediate HBx-induced cell killing suggest that HBx acts through conserved host targets (Bcl-2 family members) and conserved signaling pathways to induce cytosolic $Ca^{2+}$ elevation, cell killing, and other cellular and viral events. They also demonstrate the unique advantage of the C. elegans genetic system for unambiguous determination of in vivo protein interaction and target identification, a daunting task in complex mammalian systems.

One of the signaling events associated with HBx expression in hepatocytes is elevation of cytosolic $Ca^{2+}$, which is critical for HBV replication, transcription and core assembly and is involved in activation of cell death and several other signaling pathways. Although the cellular target of HBx-mediated calcium stimulation is unknown, HBx has been proposed to target mitochondria to effect permeability transition, which plays an important role in regulating intracellular $Ca^{2+}$ homeostasis. In this study, the present inventors have shown that HBx interacts directly with CED-9, a mitochondrial protein, to increase cytosolic $Ca^{2+}$, which then triggers activation of necrosis in C. elegans through $Ca^{2+}$-dependent proteases (CLP-1 and TRA-3). CED-9-dependent $Ca^{2+}$ elevation and necrosis induced by HBx can both be suppressed by CsA, an inhibitor of MPT. These results are consistent with the observations in human cells that HBx acts through MPT to control intracellular calcium, cell death, and HBV replication and indicate that CED-9 is the cellular target of HBx in elevating intracellular $Ca^{2+}$. Since Bcl-2 associates with HBx in HBV-infected hepatocytes, can substitute for CED-9 in mediating HBx-induced cell killing in C. elegans, and has been implicated in regulating mitochondria permeability transition, Bcl-2 and Bcl-xL, both of which are mitochondrial proteins, are likely targeted by HBx during HBV infection to alter $Ca^{2+}$ signaling. The induced cytosolic $Ca^{2+}$ increase then triggers activation of multiple viral and host events, including HBV replication, assembly and cell death. Therefore, targeting the BH3-like motif of HBx to prevent HBx binding to Bcl-2 family proteins could be a new and ideal therapeutic strategy for treating HBV-related liver disorders without perturbing host cell signaling pathways.

Example 3

Microscale liquid culture of *C. elegans*. Peptaibol TK was mixed with the S-medium to form 70% peptaibol TK concentration solution. This mixture was placed in 96-well culture plate, along with worms and pure S-medium (wormbook, maintenance of *C. elegans*) as control. Centrifugal sedimentation of HB101 was suspended by culture liquid as *C. elegans* food supply in 1:1 volume rate.

Embryo/germline cell corpse counting assay. Embryo and germline cell corpse were counted under DIC field of Zeiss Nomarski microscope. For embryo cell corpse counting, late LA worms were transferred into microscale liquid culture and their egg lay in 24 hours were scored for cell corpses. For germline cell corpse counting, middle L4 worms were transferred into microscale liquid culture and counted their germline cell corpse at 24 hours and 48 hours post liquid culture. The alleles used in cell corpse counting assay were egl-1(n3082), ced-9(n1950), ced-4(n1162) and ced-1 (e1735).

Gonad dissection. Gonad dissection was performed on smIs203 worms, which carry an integrated CED-4::GFP transgene. Worms were dissected on common glass slide. After anaesthetizing worms with 10 µL of 30 µM sodium azide, more 30 µL M9 was added for dilution. To dissect the gonad, the worm's head was placed between two syringe needles and decapitate by moving needles in a scissors motion. Then, released gonad was observed after covering with cover glass.

Results

Figure 1C:
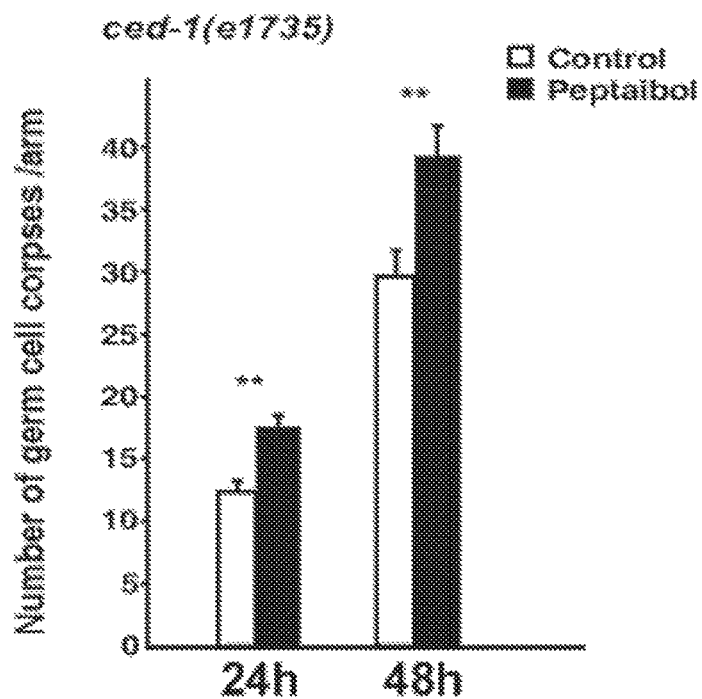
FIG. 1c is a bar graph showing peptaibol TK causes more persistent cell corpses in the germline of ced-1(e1735) animals. Germ cell corpses in animals 24 hour and 48 hour post L4 to the adult molt were scored (n=30).
Figure 1E:
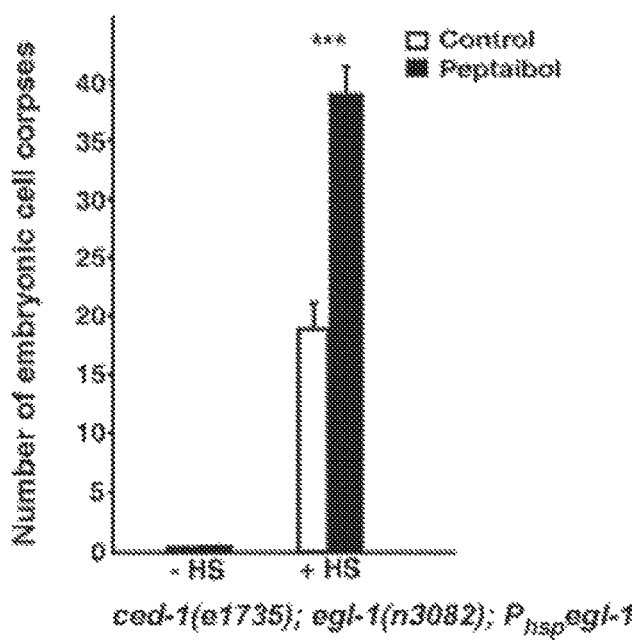
FIG. 1e is a bar graph showing peptaibol TK can synergize with EGL-1 to induce apoptosis. ced-1(e1735); egl-1 (n3082); smIs82 animals were treated with peptaibol TK and subjected to heat-shock treatment. Two-fold stage embryos were scored for cell corpses. smIs82 is an integrated transgene carrying $P_{hsp}$EGL-1. Data are means±SEM. More than 20 embryos (b, d, e) or 30 animals (c) were scored in each experiment.  P<0.01; * P<0.001.

In order to understand how peptaibol TK selectively promotes apoptosis in human cancer cells, apoptosis in *C. elegans* was tested using a mixture of peptaibol TK VI (SEQ ID: NO 1), peptaibol TK VII (SEQ ID: NO 2) and peptaibol TK VIII (SEQ ID: NO 3). See FIG. 1a. *C. elegans* animals were cultured in 96-well plates in S medium containing 20 µM peptaibol TK and the number of apoptotic cell corpses in *C. elegans* embryos and germline were counted. To sensitize the cell death assay, ced-1(e1735) animals, in which engulfment of apoptotic cells is blocked, were used to allow easy scoring of apoptotic cells. It was found that compared to the buffer control peptaibol TK treatment caused significantly more apoptotic cell corpses in both ced-1(e1735) embryos and germline (FIGS. 1a-c), indicating that peptaibol TK can induce ectopic apoptosis in *C. elegans*.

To investigate how peptaibol TK induces ectopic cell death, the genetic requirement for peptaibol TK-induced cell death was examined. The central cell killing pathway in *C. elegans* is mediated by a negative regulatory cascade, in which the cell death initiator EGL-1 induces cell death by antagonizing the activity of CED-9, a cell death inhibitor, which allows the caspase activator CED-4 to activate the cell killing caspase CED-3 (FIG. 1f). It was found that a strong loss-of-function (lf) mutation in ced-4 (n1162) or ced-3 (n2433) completely blocked peptaibol TK-induced ectopic cell death in both ced-1(e1735) embryos and germline (FIG. 1d). These results indicate that peptaibol TK acts upstream of or in parallel to ced-4 to induce apoptosis. Similarly, a strong lf mutation in egl-1 (n3082) completely blocked peptaibol TK-induced ectopic cell death in ced-1 (e1735) embryos (FIG. 1d). Interestingly, a gain-of-function (gf) mutation in ced-9 (n1950) causes a Gly169 to Glu substitution in the BH3-motif binding pocket of the CED-9 protein that blocks binding of the BH3-only protein EGL-1 to CED-9 and thus EGL-1 induced release of CED-4 from the inhibitory CED-4/CED-9 complex tethered on the outer membrane of mitochondria. Like egl-1(n3082), ced-9 (n1950) blocked peptaibol TK-induced ectopic cell death in ced-1(e1735) embryos (FIG. 1d). These results indicate that peptaibol TK acts upstream of or in parallel to CED-9 and could target CED-9 directly to induce apoptosis.

Since release of CED-4 from the inhibitory CED-4/CED-9 complex is a key event in *C. elegans* apoptosis, whether peptaibol TK promotes CED-4 release to induce apoptosis was investigated. It has been reported that during apoptosis CED-4 disassociates from mitochondria and translocates to the perinuclear region in apoptotic cells. A low-copy integrated transgene (smIs203) carrying a translational CED-4::GFP fusion under the control of the endogenous ced-4 promoter was generated. In dissected gonad from smIs203 animals, CED-4::GFP displayed predominantly punctuate cytoplasmic staining characteristic of mitochondria localization. Staining with MitoTracker Red, a mitochondria-specific dye, confirmed that CED-4::GFP co-localized with MitoTracker Red to mitochondria. Treatment of peptaibol TK resulted in loss of cytoplasmic staining and appearance of GFP rings, which indicate translocation of CED-4::GFP from mitochondria to the nuclear membrane. These results indicate that peptaibol TK can promote apoptotic CED-4 release in vivo.

Whether peptaibol TK can promote CED-4 release in vitro was also examined. In this experiment, peptaibol TK was incubated with the CED-4/CED-9 complex in the presence or absence of limited amount of EGL-1, which alone was barely able to release CED-4 from the CED-4/CED-9 complex. Although peptaibol TK alone was incapable of causing release of CED-4, it greatly enhanced the release of CED-4 in combination with EGL-1. Thus, peptaibol TK can cooperate with EGL-1 to promote release of CED-4 from the CED-4/CED-9 complex and thus apoptosis.

The enhanced EGL-1-induced release of CED-4 from the CED-4/CED-9 complex by peptaibol TK was examined using the gel-filtration assay. When 7 nmol of the CED-4/CED-9 complexes were loaded on the Superdex 200 column, the complex was eluted in a single peak. When the same amount of CED-4/CED-9 complexes were pre-incubated with 12 nmol of EGL-1 and then loaded on the Superdex column, a minor second peak consistent with the size of CED-4 tetramer was observed, indicating limited amount of CED-4 release from the CED-4/CED-9 complex. Although pre-incubation of the same amount of CED-4/CED-9 complexes with 150 nmol of peptaibol TK did not cause any detectable CED-4 release, pre-incubation of 150 nmol of peptaibol TK and 150 nmol of EGL-1 with the CED-4/CED-9 complexes caused a major shift of the CED-4/CED-9 protein peak to the CED-4 tetramer peak, indicating a greatly increased release of CED-4 from the CED-4/CED-9 complexes. Taken together, these in vitro CED-4 releasing results suggest that peptaibol TK promotes apoptosis by enhancing EGL-1-induced release of CED-4 from the inhibitory CED-4/CED-9 complex and are consistent with the observations that peptaibol TK failed to induce cell death in egl-1(n3082) embryos (FIG. 1d).

To probe how peptaibol TK enhances EGL-1-induced release of CED-4 from the CED-4/CED-9 complex, whether peptaibol TK interacts with EGL-1, CED-9, or both was tested using isothermal titration calorimetry (ITC) assays. When peptaibol TK was used to titrate CED-9, the well-correlated differential heating power and the molar ratio between peptaibol TK and CED-9 indicate a weak but detectable interaction with a binding affinity ($K_B$) at $4.26\times10^4$ $M^{-1}$. By contrast, titration of EGL-1 with peptaibol TK showed scattered data points with small variations, which is indicative of background thermal fluctuations and no significant interaction between EGL-1 and peptaibol TK. As expected, CED-9 interacted with EGL-1 strongly, yielding a binding affinity of $4.04\times10^6$ $M^{-1}$. When CED-9 was pre-incubated with peptaibol TK before being titrated with EGL-1, a much stronger binding affinity ($1.52\times10^8$ $M^{-1}$) was detected, which is approximately 38 folds of that between CED-9 and EGL-1. Given that peptaibol TK didn't bind EGL-1, this great enhancement in binding affinity between EGL-1 and CED-9 is likely caused by interaction of peptaibol TK with CED-9, which may induce an allosteric change in CED-9 that greatly enhances its binding to EGL-1. This is also consistent with the observation that peptaibol TK enhances EGL-1-induced release of CED-4 from the CED-4/CED-9 complex both in vitro and in vivo.

The Hepatitis B Virus X protein, HBx, has been shown to play a critical role in pathogenesis and neoplastic transformation of hepatocytes in HBV-infected patients. Interestingly, HBx interacts with highly conserved host targets, the Bcl-2 family cell death inhibitors, through a BH3-like motif to promote intracellular calcium increase, leading to apoptosis, necrosis and viral replication. Since HBx induces both apoptotic and necrotic cell death in *C. elegans* through interacting with CED-9, whether peptaibol TK similarly enhances HBx-induced cell death in *C. elegans* was tested using smIs98 animals, which carry an integrated transgene that expresses HBx and GFP under the control of the touch-cell-specific mec-7 and mec-3 gene promoters ($P_{mec-7}$HBx and $P_{mec-3}$GFP), respectively. In smIs98 animals treated with peptaibol TK, the percentage PLM touch cell death is 71%, which is significantly higher than (52%) that observed in smIs98 animals treated with buffer control (FIG. 2). On the other hand, peptaibol TK or buffer control treatment of smIs3 animals, which carry an integrated transgene containing only $P_{mec-3}$GFP and without $P_{mec-7}$HBx, resulted in a similar low percentage of PLM cell killing (FIG. 2). Similar results were obtained when $P_{mec-7}$HBx was present as an extrachromosomal array in bzIs8 animals, which carry an integrated transgene containing $P_{mec-4}$GFP that also label touch cells specifically with GFP (FIG. 2). These results indicate that peptaibol TK can enhance HBx-induced cell death in *C. elegans*, just as it does in enhancing EGL-1-induced cell death.

Because HBx promotes cell killing in *C. elegans* and in human hepatocytes through conserved host targets, the Bcl-2 family cell death inhibitors, whether peptaibol TK can promote increased cell killing in HBV-transfected human hepatocytes was tested. HepG2-N10 cells, which are human hepatic cells carrying an integrated copy of 140% head-to-tail HBV genome (pHBV), and control HepG2 cells were treated with various concentration of peptaibol TK. Increasing concentrations (4, 8, 12, 16 μM) of peptaibol TK did not seem to significantly alter the cell density of the control HepG2 cells, but significantly reduced the cell density of the HepG2-N10 cells, suggesting that peptaibol TK promotes increased cell killing in HBV-transfected hepatic cells, but not in uninfected HepG2 cells. The effect of peptaibol TK on C57BL/6 mice carrying an integrated copy of pHBV and control C57BL/6 mice were tested through intraperitoneal injection. Compared to the control C57BL/6 mice, HBV transgenic mice are more sensitive to the peptaibol TK injection, as the serum Alanine Aminotransferase (ALT) levels, an indicator of liver damage, are higher in HBV transgenic mice than the control mice six hours post IP injection. These results provide preliminary supporting evidence that peptaibol TK promotes increased cell killing selectively in HBV-transfected hepatocytes.

Discussion

Similar to the situation in cultured cell, peptaibol TK induced cell death in *C. elegans* through the apoptosis pathway. Genetic analysis indicated that peptaibol TK works cooperatively with EGL-1 to kill cell by apoptosis. To prove this hypothesis, experiment was performed which showed that peptaibol TK indeed promoted more CED-4 release in vivo and in vitro, where the EGL-1 is present, to enhance the apoptosis-inducing effect. Further, ITC was used to investigate the minutiae of interaction process among peptaibol TK, EGL-1 and CED-9/CED-4 complex. Based on the experimental data, it appears firstly, peptaibol TK binds to CED-9 of CED-9/CED-4 complex in a thermodynamically unsteady manner. Peptaibol TK binding is believed to change the conformation of CED-9, turning it into a state that has a higher affinity for EGL-1 and thus greatly facilitating EGL-1-induced release of CED-4.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A method for treating hepatitis B infection in a subject, comprising administering to the subject a therapeutically effective amount of a peptaibol TK selected from peptaibol TK VI (SEQ ID NO:1), peptaibol TK VII (SEQ ID NO:2), peptaibol TK VIII (SEQ ID NO:3), or a derivative thereof, or a mixture thereof.

2. The method of claim 1, wherein the peptaibol TK derivative is a peptaibol in which at least one amino acid of the natural peptaibol TK sequence has been substituted by other amino acids, and maintains an in vitro activity within 25% of a wild type peptaibol TK.

3. The method of claim 1, wherein the peptaibol TK derivative is a peptaibol modified at the N- or C-terminal end of the peptide sequence of peptaibol TK and have an in vitro activity within 25% of a wild type peptaibol TK.

4. The method of claim 3, wherein the peptaibol TK derivative is an ester of a peptaibol TK selected from peptaibol TK VI (SEQ ID NO:1), peptaibol TK VII (SEQ ID NO:2), and peptaibol TK VIII (SEQ ID NO:3).

5. The method of claim 3, wherein the peptaibol TK derivative is an amide of a peptaibol TK selected from peptaibol TK VI (SEQ ID NO:1), peptaibol TK VII (SEQ ID NO:2), and peptaibol TK VIII (SEQ ID NO:3).

6. The method of claim 3, wherein the peptaibol TK derivative is a pegylated peptaibol TK selected from peptaibol TK VI (SEQ ID NO:1), peptaibol TK VII (SEQ ID NO:2), and peptaibol TK VIII (SEQ ID NO:3).

7. The method of claim 1, wherein the peptaibol TK derivative is a peptaibol comprising at least one modification that prevents the destruction of the peptaibol by proteases or peptidases.

8. The method of claim 1, wherein the peptaibol TK derivative is a peptaibol comprising at least one conservative substitution of an amino acid compared to the wild type sequence of peptaibol TK selected from peptaibol TK VI (SEQ ID NO:1), peptaibol TK VII (SEQ ID NO:2), and peptaibol TK VIII (SEQ ID NO:3).

* * * * *